United States Patent
Deslauriers

(10) Patent No.: US 11,458,298 B2
(45) Date of Patent: Oct. 4, 2022

(54) ASSEMBLIES CONTAINING TWO CONDUCTIVE GEL COMPOSITIONS AND METHODS OF PRODUCTION AND USE THEREOF

(71) Applicant: Novocure GmbH, Root (CH)

(72) Inventor: Richard Deslauriers, Woodbury, CT (US)

(73) Assignee: Novocure GmbH

(*) Notice: Subject to any disclaimer, the term of this patent is extended or adjusted under 35 U.S.C. 154(b) by 36 days.

(21) Appl. No.: 17/155,394

(22) Filed: Jan. 22, 2021

(65) Prior Publication Data

US 2021/0220640 A1     Jul. 22, 2021

Related U.S. Application Data

(60) Provisional application No. 63/004,016, filed on Apr. 2, 2020, provisional application No. 62/964,275, filed on Jan. 22, 2020.

(51) Int. Cl.
*A61N 1/00* (2006.01)
*A61N 1/04* (2006.01)
*A61N 1/36* (2006.01)
*B06B 1/06* (2006.01)

(52) U.S. Cl.
CPC ....... *A61N 1/0496* (2013.01); *A61N 1/36002* (2017.08); *B06B 1/0607* (2013.01)

(58) Field of Classification Search
CPC .................. A61N 1/0496; A61N 1/36002
See application file for complete search history.

(56) References Cited

U.S. PATENT DOCUMENTS

| | | | |
|---|---|---|---|
| 5,974,344 A * | 10/1999 | Shoemaker, II | A61N 1/0468 607/152 |
| 7,565,205 B2 | 7/2009 | Palti | |
| 8,715,203 B2 * | 5/2014 | Palti | A61N 1/0472 600/556 |
| 2007/0093788 A1 | 4/2007 | Carter | |
| 2019/0160281 A1 * | 5/2019 | Del Rossi | A61N 1/36034 |

OTHER PUBLICATIONS

International Search Report in PCT/US2021/014590, dated May 7, 2021.
Written Opinion of the International Searching Authority in PCT/US2021/014590, dated May 7, 2021.

* cited by examiner

*Primary Examiner* — John R Downey
*Assistant Examiner* — Anant A Gupta
(74) *Attorney, Agent, or Firm* — Dunlap Codding, P.C.

(57) ABSTRACT

An assembly for use in a TTField-generating system is disclosed that includes at least one electrode in combination with a polymerized conductive hydrogel and a liquid conductive hydrogel disposed on at least a portion of the polymerized hydrogel. Also disclosed are transducer arrays including the assemblies, as well as kits and methods of producing and using the assemblies, arrays, and systems.

20 Claims, 8 Drawing Sheets ated electric fields within the intermediate frequency range (100-500 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441, 776. TTFields are typically delivered through two pairs of transducer arrays that generate perpendicular fields within the treated tumor; the electrode arrays that make up each of these pairs are positioned on opposite sides of the body part that is being treated. More specifically, for the OPTUNE® system, one pair of electrodes is located to the left and right (LR) of the tumor, and the other pair of electrodes is located anterior and posterior (AP) to the tumor. TTFields are approved for the treatment of glioblastoma multiforme (GBM), and may be delivered, for example, via the OPTUNE® system (Novocure Limited, St. Helier, Jersey), which includes transducer arrays placed on the patient's shaved head.

ASSEMBLIES CONTAINING TWO CONDUCTIVE GEL COMPOSITIONS AND METHODS OF PRODUCTION AND USE THEREOF

CROSS REFERENCE TO RELATED APPLICATIONS/INCORPORATION BY REFERENCE STATEMENT

This application claims benefit under 35 USC § 119(e) of U.S. Provisional Application No. 62/964,275, filed Jan. 22, 2020; and U.S. Provisional Application No. 63/004,016, filed Apr. 2, 2020. The entire contents of the above-referenced patent applications are hereby expressly incorporated herein by reference.

STATEMENT REGARDING FEDERALLY SPONSORED RESEARCH OR DEVELOPMENT

Not Applicable.

BACKGROUND

Tumor Treating Fields (TTFields or TTFs) are low intensity (e.g., 1-3 V/cm) alternating electric fields within the intermediate frequency range (100-500 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the electrode arrays that make up each of these pairs are positioned on opposite sides of the body part that is being treated. More specifically, for the OPTUNE® system, one pair of electrodes is located to the left and right (LR) of the tumor, and the other pair of electrodes is located anterior and posterior (AP) to the tumor. TTFields are approved for the treatment of glioblastoma multiforme (GBM), and may be delivered, for example, via the OPTUNE® system (Novocure Limited, St. Helier, Jersey), which includes transducer arrays placed on the patient's shaved head.

Each transducer array used for the delivery of TTFields in the OPTUNE® device comprises a set of ceramic disk electrodes, which are coupled to the patient's skin (such as, but not limited to, the patient's shaved head for treatment of GBM) through a layer of conductive medical gel. The purpose of the medical gel is to deform to match the body's contours and to provide good electrical contact between the arrays and the skin; as such, the gel interface bridges the skin and reduces interference. The device is intended to be continuously worn by the patient for 2-4 days before removal for hygienic care and re-shaving (if necessary), followed by reapplication with a new set of arrays. As such, the medical gel remains in substantially continuous contact with an area of the patient's skin for a period of 2-4 days at a time, and there is only a brief period of time in which the area of skin is uncovered and exposed to the environment before more medical gel is applied thereto.

Various types of medical gels are known in the art. One particular type of gel useful as part of a TTField-generating system is a conductive hydrogel. Hydrogels are three-dimensional (3-D) networks of hydrophilic polymers that can swell in water and hold a large amount of water while maintaining their structure due to chemical or physical cross-linking of individual polymer chains. Hydrogels are used in many fields, which include the medical sciences if the hydrogels are nontoxic and compatible with biological environments. (Bahram et al. (2016) "An Introduction to Hydrogels and Some Recent Applications." *Emerging Concepts in Analysis and Applications of Hydrogels*. InTech Open).

However, dermatologic adverse events (dAEs) have been observed with the use of existing medical grade hydrogels with TTField generating systems at an incidence rate of 16% and 22% in the phase III trial and the post-marketing surveillance program, respectively; these dAEs include (but are not limited to) allergic and irritant dermatitis, mechanical lesions, ulcers, and skin infections. In particular, irritant contact dermatitis and allergic contact dermatitis can arise from chemical irritation from and allergy to the hydrogel, respectively, while maceration of the skin due to prolonged exposure to the hydrogel can cause lesions/ulcers on the skin, and these lesions/ulcers are subsequently susceptible to infection. These adverse events are exacerbated by the requirement that the hydrogel remain in continuous contact with the patient's skin for multiple days at a time without an extended period of "breathability" between application of TTField arrays to the skin. (Lacouture et al. (2014) *Seminars in Oncology*, 41:S1-S14).

Currently available medical hydrogels typically have pH's that are too acidic for long term wear and thus are damaging to the skin upon extended exposure thereto. In addition, the bottom liner adhesion (i.e., skin adhesion) rate for the currently available hydrogels typically is not high enough to provide the necessary level of attachment to skin for the wear time required. Also, adjustment of either of these two properties can increase the resistivity of the hydrogel, thus affecting the ability of the hydrogel to pass electrical current therethrough. In addition, when a hydrogel comes into contact with sweat over the wear period, the hydrogel swells and degrades, which increases resistivity. Further, loss of the hydrogel interface over the approximately three-day wear period (such as, but not limited to, by erosion of the adhesiveness and conductivity of the hydrogel) reduces the standard current/electric field generated by the TTField system and thus decreases the functionality and overall effectiveness of the TTField treatment.

Because of this extended exposure and the concomitant unique usage of hydrogels with the TTField system, new and improved conductive gel formulations and assemblies containing same are desired that possess multiple properties that are unique and vary from the properties typically possessed by currently available medical grade hydrogels. It is to such assemblies, as well as kits and transducer arrays containing same and methods of producing and using same, that the present disclosure is directed.

DETAILED DESCRIPTION

Figure 1:
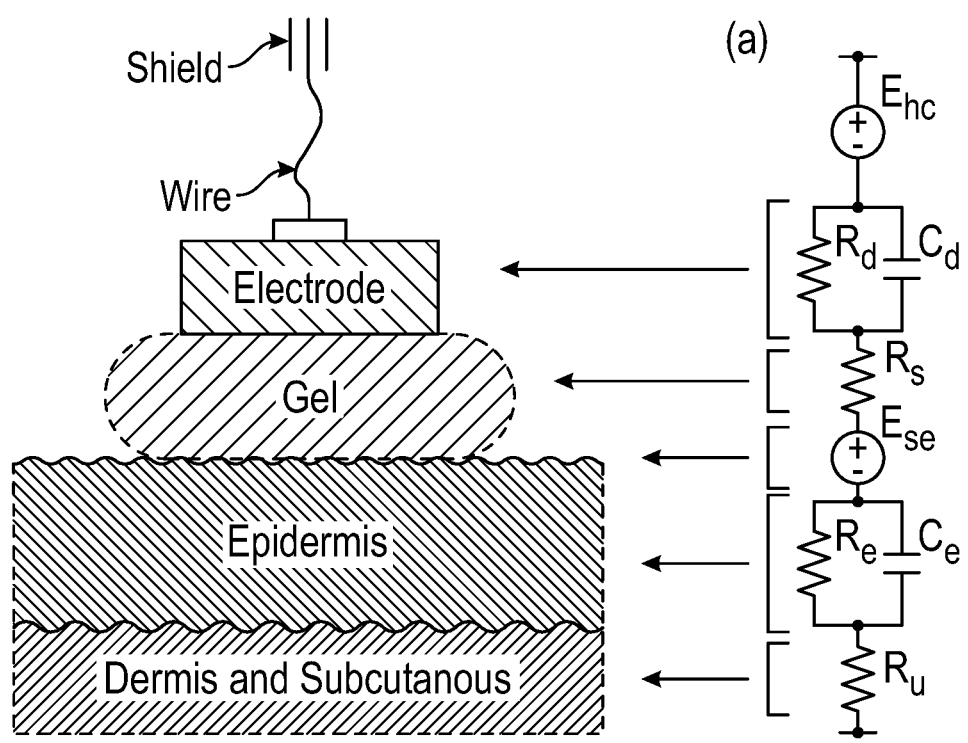
FIG. 1 is a schematic representation of a general electrode conductive gel assembly disposed upon a patient's skin, in which the conductive gel provides an adhesion interface between the electrode and a patient's skin.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, assemblies, systems, kits, and/or methods disclosed herein can be made and executed without undue experimentation in light of the present disclosure. While the compositions, assemblies, systems, kits, and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "polypeptide" as used herein will be understood to refer to a polymer of amino acids. The polymer may include d-, l-, or artificial variants of amino acids. In addition, the term "polypeptide" will be understood to include peptides, proteins, and glycoproteins.

The term "polynucleotide" as used herein will be understood to refer to a polymer of two or more nucleotides. Nucleotides, as used herein, will be understood to include deoxyribose nucleotides and/or ribose nucleotides, as well as artificial variants thereof. The term polynucleotide also includes single-stranded and double-stranded molecules.

The terms "analog" or "variant" as used herein will be understood to refer to a variation of the normal or standard form or the wild-type form of molecules. For polypeptides or polynucleotides, an analog may be a variant (polymorphism), a mutant, and/or a naturally or artificially chemically modified version of the wild-type polynucleotide (including combinations of the above). Such analogs may have higher, full, intermediate, or lower activity than the normal form of the molecule, or no activity at all. Alternatively and/or in addition thereto, for a chemical, an analog may be any structure that has the desired functionalities (including alterations or substitutions in the core moiety), even if comprised of different atoms or isomeric arrangements.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "pharmaceutically acceptable" refers to compounds and compositions which are suitable for administration to humans and/or animals without undue adverse side effects such as (but not limited to) toxicity, irritation, and/or allergic response commensurate with a reasonable benefit/risk ratio.

The term "pharmaceutically-acceptable excipient" refers to any carrier, vehicle, and/or diluent known in the art or otherwise contemplated herein that may improve solubility, deliverability, dispersion, stability, and/or conformational integrity of the compositions disclosed herein.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

The term "treatment" refers to both therapeutic treatment and prophylactic or preventative measures. Those in need of treatment include, but are not limited to, individuals already having a particular condition/disease/infection as well as individuals who are at risk of acquiring a particular condition/disease/infection (e.g., those needing prophylactic/preventative measures). The term "treating" refers to administering an agent/element/method to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

Administering a therapeutically effective amount or prophylactically effective amount is intended to provide a therapeutic benefit in the treatment, prevention, and/or management of a disease, condition, and/or infection. The specific amount that is therapeutically effective can be readily determined by the ordinary medical practitioner, and can vary depending on factors known in the art, such as (but not limited to) the type of condition/disease/infection, the patient's history and age, the stage of the condition/disease/infection, and the co-administration of other agents.

The term "effective amount" refers to an amount of a biologically active molecule or conjugate or derivative thereof, or an amount of a treatment protocol (i.e., an alternating electric field), sufficient to exhibit a detectable therapeutic effect without undue adverse side effects (such as (but not limited to) toxicity, irritation, and allergic response) commensurate with a reasonable benefit/risk ratio when used in the manner of the inventive concept(s). The therapeutic effect may include, for example but not by way of limitation, preventing, inhibiting, or reducing the occurrence of at least one tumor and/or cancer. The effective amount for a subject will depend upon the type of subject, the subject's size and health, the nature and severity of the condition/disease/infection to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the condition/disease/infection in conjunction with the treatments of the present disclosure. This concurrent therapy can be sequential therapy, where the patient is treated first with one treatment protocol/pharmaceutical composition and then the other treatment protocol/pharmaceutical composition, or the two treatment protocols/pharmaceutical compositions are given simultaneously.

The terms "administration" and "administering," as used herein, will be understood to include all routes of administration known in the art, including but not limited to, oral, topical, transdermal, parenteral, subcutaneous, intranasal, mucosal, intramuscular, intraperitoneal, intravitreal, and intravenous routes, and including both local and systemic applications. In addition, the compositions of the present disclosure (and/or the methods of administration of same) may be designed to provide delayed, controlled, or sustained release using formulation techniques which are well known in the art.

Turning now to the inventive concept(s), certain non-limiting embodiments thereof include the use of a combination of two conductive hydrogel compositions—one semi-solid and one liquid—for application to a patient's skin during treatment, such as (but not limited to) with a TTField-generating system. The addition of a hypoallergenic liquid hydrogel to an electrode-polymerized hydrogel assembly of a transducer array of a TTField-generating system provides at least three advantages over the prior art. First, the liquid hydrogel enhances wetting of the surfaces of the polymerized hydrogel and the skin without dramatically impacting the adhesion between the polymerized hydrogel and the skin surface. Second, the liquid hydrogel disposed between the polymerized hydrogel and a patient's skin serves to further enhance the polymerized hydrogel-skin interface without dramatically affecting skin conductivity. Third, the liquid hydrogel serves as a skin barrier that decreases the occurrence of dermatologic adverse events (dAEs) that are typically observed with the use of existing medical grade hydrogels with TTField generating systems.

Certain non-limiting embodiments of the present disclosure are directed to an assembly (for use in, for example but not by way of limitation, a transducer array of a TTField-generating system) that includes at least one electrode, a polymerized conductive hydrogel, and a liquid conductive hydrogel. The polymerized hydrogel is for placement between the at least one electrode and a patient's skin and has a first surface and a second surface; the first surface of the polymerized hydrogel adheres to a surface of the at least one electrode, and the second surface of the polymerized hydrogel is for application to a patient's skin. The liquid hydrogel is disposed on at least a portion of the second surface of the polymerized hydrogel and interfaces the polymerized hydrogel with the patient's skin.

The assembly may optionally further include a liner that is disposed on the liquid hydrogel and that covers at least a portion of the second surface of the polymerized hydrogel to maintain the liquid hydrogel in place on the polymerized hydrogel and/or to maintain the sterility thereof until use.

Any type of conductive or non-conductive electrode(s) that can be utilized for generating TTFields that are known in the art or otherwise contemplated herein may be utilized in accordance with the present disclosure. Examples of non-conductive electrodes (and transducer arrays containing same) that function as part of a TTField system are known in the art and are described, for example but not by way of limitation, in U.S. Pat. Nos. 7,016,725; 7,089,054; 7,333,852; 7,565,205; 8,244,345; 8,715,203; 8,764,675; 10,188,851; and 10,441,776; and in US Patent Application Nos. US 2018/0160933; US 2019/0117956; US 2019/0307781; and US 2019/0308016. For example, in certain non-limiting embodiments, the electrode may be an insulated electrode that comprises at least one non-conducting layer, at least one conducting layer, and a high capacitance layer having an upper surface and a lower surface; in addition, at least one opening may be disposed between the upper surface and the lower surface of the high capacitance layer. When this electrode structure is utilized, the first surface of the polymerized hydrogel is adhered to lower surface of the high capacitance layer of the electrode.

Alternatively (and/or in addition thereto), the at least one electrode of the assemblies may be formed of ceramic materials or non-ceramic dielectric materials positioned over a flat conductor. Examples of the latter include polymer films disposed over pads on a printed circuit board or over flat pieces of metal. Other non-limiting examples of electrodes that can be utilized in accordance with the present disclosure include electrodes that are not capacitively coupled; in this situation, the at least one electrode is implemented using a region of a conductive material that is configured for placement against a person's body, with no insulating dielectric layer disposed between the conductive element and the body. Examples of the conductive material include, but are not limited to, a conductive film, a conductive fabric, and/or a conductive foam. Other alternative constructions of electrodes may be utilized in accordance with the present disclosure, as long as they are capable of delivering TTFields to the person's body as described herein.

In certain particular (but non-limiting) embodiments, the electrode generates an alternating electric field within a target region of the patient. The target region typically comprises at least one tumor, and the generation of the alternating electric field selectively destroys or inhibits growth of the tumor. The alternating electric field may be generated at any frequency that selectively destroys or inhibits growth of the tumor. For example (but not by way of limitation), the alternating electric field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 400 kHz, about 425 kHz, about 450 kHz, about 475 kHz, or about 500 kHz, as well as a range formed from any of the above values (i.e., a range of from about 50 kHz to about 500 kHz, a range of from about 100 kHz to about 150 kHz, a range of from about 150 kHz to about 300 kHz, etc.), and a range that combines two integers that fall between two of the above-referenced values (i.e., a range of from about 32 kHz to about 333 kHz, a range of from about 78 kHz to about 298 kHz, etc.).

In certain particular (but non-limiting) embodiments, the alternating electric field may be imposed at two or more different frequencies. When two or more frequencies are present, each frequency is selected from any of the above-referenced values, or a range formed from any of the above-referenced values, or a range that combines two integers that fall between two of the above-referenced values.

Each of the polymerized conductive hydrogel and the liquid hydrogel may be in any form that allows the assembly to function in accordance with the present disclosure. In certain particular (but non-limiting) embodiments, each of the hydrogels is sterile. In addition, in certain non-limiting embodiments, each of the hydrogels will not substantially degrade upon exposure to sterilization conditions that include gamma rays or ethylene oxide gas.

In certain particular (but non-limiting) embodiments, the polymerized hydrogel is semi-solid.

The polymerized hydrogel may be formed of any hydrophilic polymer that allows the hydrogel to function in accordance with the present disclosure. For example (but not by way of limitation), the hydrogel may be a polyacrylic acid gel, a povidone gel, or a cellulose gel. In addition, the hydrogel may comprise at least one of chitosan, alginate, agarose, methylcellulose, hyaluronan, collagen, laminin, matrigel, fibronectin, vitronectin, poly-1-lysine, proteoglycans, fibrin glue, gels made by decellularization of engineered and/or natural tissues, as well as any combinations thereof. Further, the gel may comprise at least one of polyglycolic acid (PGA), polylactic acid (PLA), poly-caprolactone (PCL), polyvinyl alcohol (PVA), polyethylene glycol (PEG), methyl methacrylate, poly(methyl methacrylate) (PMMA), poly(2-hydroxyethyl methacrylate) (Poly-HEMA), poly(glycerol sebacate), polyurethanes, poly(isopropylacrylamide), poly(N-isopropylacrylamide), or any combination thereof.

The polymers of the polymerized hydrogel may be provided with any polymer chain length that allows the gel compositions to function as described herein. For example (but not by way of limitation), the polymer chain length may be about 1 nm, about 2 nm, about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, and above, as well as a range that combines any two of the above-referenced values (i.e., a range of from about 3 nm to about 175 nm, a range of from about 5 nm to about 150 nm, or a range of from about 10 nm to about 125 nm, a range of from about 15 nm to about 100 nm, etc.), and a range that combines two integers that fall between two of the above-referenced values (i.e., a range of from about 3 nm to about 157 nm, etc.).

In other non-limiting embodiments, the range of the polymer chain length is dependent upon the frequency(ies) of the alternating electric field. For example (but not by way of limitation), the range of the polymer chain length may be based upon a range of frequencies of the alternating electric field. Non-limiting examples include a range of from about 5 nm to about 50 nm when the alternating electric field has a frequency in a range of from about 50 kHz to about 150 kHz, a range of from about 50 nm to about 100 nm when the alternating electric field has a frequency in a range of from about 150 kHz to about 300 kHz, etc.

The polymerized hydrogel may be provided with any pH that does not damage the skin of a patient or cause chemical irritation of the skin upon prolonged exposure to the gel. For example (but not by way of limitation), the gel may have a pH of about 6, about 6.5, about 7, about 7.5, about 8, as well as a range formed from any of the above values (i.e., a range of from about 6 to about 8, a range of from about 6.5 to about 7.5, etc.).

The polymerized hydrogel may be provided with any level of volume resistivity that maximizes the conductiveness of the gel. For example (but not by way of limitation), the gel may have a volume resistivity of less than about 100 Ohm-in, less than about 95 Ohm-in, less than about 90 Ohm-in, less than about 85 Ohm-in, less than about 80 Ohm-in, less than about 75 Ohm-in, less than about 70 Ohm-in, less than about 65 Ohm-in, less than about 60 Ohm-in, less than about 55 Ohm-in, less than about 50 Ohm-in, less than about 45 Ohm-in, less than about 40 Ohm-in, less than about 35 Ohm-in, less than about 30 Ohm-in, less than about 25 Ohm-in, less than about 20 Ohm-in, less than about 15 Ohm-in, less than about 10 Ohm-in, or lower, as well as a range formed of any of the above values (i.e., a range of from about 10 Ohm-in to about 100 Ohm-in, etc.) and a range that combines two integers that fall between two of the above-referenced values (i.e., a range of from about 13 Ohm-in to about 96 Ohm-in, etc.).

The polymerized hydrogel may be provided with any thickness that allows the gel to function in accordance with the present disclosure. Non-limiting examples of thicknesses that may be utilized in accordance with the present disclosure include about 1 mil, about 5 mil, about 10 mil, about 15 mil, about 20 mil, about 25 mil, about 30 mil, about 35 mil, about 40 mil, about 45 mil, about 50 mil, about 55 mil, about 60 mil, about 65 mil, about 70 mil, about 75 mil, about 80 mil, about 85 mil, about 90 mil, about 95 mil, about 100 mil, or higher, as well as a range that combines any two of the above-referenced values (i.e., a range of from about 10 mil to about 50 mil, etc.), and a range that combines two integers that fall between two of the above-referenced values (i.e., a range of from about 12 mil to about 48 mil, etc.).

The polymerized hydrogel may be provided with any skin adhesion rate that allows the gel to function in accordance with the present disclosure. For example (but not by way of limitation), the skin adhesion rate of the gel may be at least about 100 g/inch, at least about 110 g/inch, at least about 120 g/inch, at least about 130 g/inch, at least about 140 g/inch, at least about 150 g/inch, at least about 160 g/inch, at least about 170 g/inch, at least about 180 g/inch, at least about 190 g/inch, at least about 200 g/inch, at least about 210 g/inch, at least about 220 g/inch, at least about 230 g/inch, at least about 240 g/inch, at least about 250 g/inch, at least about 260 g/inch, at least about 270 g/inch, at least about 280 g/inch, at least about 290 g/inch, at least about 300 g/inch, or higher, as well as a range of any of the above values (a range of from about 120 g/inch to about 300 g/inch, etc.), and a range that combines two integers that fall between two of the above-referenced values (i.e., a range of from about 115 g/inch to about 295 g/inch, etc.).

In certain non-limiting embodiments, the polymerized hydrogel has at least one of a decreased polymer chain length and an added free salt when compared to existing gel compositions; the decrease in polymer chain length and increase in free salt concentration maximizes the conductivity of the gel while reducing the occurrence of skin irritation caused by the gel. In a particular (but non-limiting) embodiment, the polymerized hydrogel comprises a free salt present via incorporation within the gel or as one layer of a multi-layered gel (i.e., a bilayered gel). The term "free salt" refers to salt molecules that are not incorporated as part of the polymerized chain structure but rather are floating substantially freely within the gel and thus are a source of free ions that conduct electricity and thus reduce impedance.

When present, the free salt present in the gel may be any salt or other substance that serves as a source of free ions that are capable of floating substantially freely within the gel, wherein the free ions serve to conduct electricity and thus reduce impedance. In certain particular (but non-limiting) embodiments, the free salt present in the gel is a source of chloride ions, citrate ions, silver ions, iodide ions, etc., or any other ions that are known to be good conductors. Non-limiting examples of free salts that may be utilized in accordance with the present disclosure are salts that contain potassium (K), ammonium ($NH^{4+}$), sodium (Na), nitrate, bicarbonate, and the like. Particular non-limiting examples of free salts that may be utilized in accordance with the present disclosure are NaCl, KCl, $CaCl_2$, $MgCl_2$, $ZnCl_2$, iodine, silver iodide (AgI), silver dihydrogen citrate (SDC), sodium dihydrogen citrate, combinations thereof, and the like.

When present, the free salt present in the gel may be provided with any concentration that allows the gel compositions to function as described herein. For example (but not by way of limitation), the free salt concentration may be at least about 0.1 mM, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1 M, or higher, as well as any range that combines any two of the above-referenced values (i.e., a range of from about 0.1 mM to about 100 mM, a range of from about 1 mM to about 50 mM, etc.), and a range that combines two integers that fall between two of the above-referenced values (i.e., a range of from about 12 mM to about 550 mM, etc.).

In other non-limiting embodiments, the free salt concentration, when present, is dependent upon the frequency(ies) of the alternating electric field. For example (but not by way of limitation), the range of the free salt concentration may be based upon a range of frequencies of the alternating electric field. Non-limiting examples include a range of from about 0.1 mM to about 50 mM when the alternating electric field has a frequency in a range of from about 50 kHz to about 150 kHz, a range of from about 50 mM to about 100 mM when the alternating electric field has a frequency in a range of from about 150 kHz to about 300 kHz, etc.

Alternatively and/or in addition thereto, in a particular non-limiting embodiment, the polymerized hydrogel comprises one or more of the following chemical and structural features/properties: a polymer chain length in a range of from about 1 nm to about 200 nm; a free salt present at a concentration in a range of from about 0.1 mM to about 1 M; a pH in a range of from about 6 to about 8; a volume resistivity of less than about 100 Ohm-in; and a skin adhesion rate of at least about 100 g/inch.

In addition, given the prolonged exposure of the polymerized gel composition to the patient's skin, the gel should be optimized for use at body temperature (i.e., in a range of from about 34° C. to about 40° C.). At these temperatures, any perforations present (as described in detail below) will introduce air flow that maximizes evaporative cooling, thereby allowing for a reduced operating temperature and cooling effect to the patient's skin.

In certain particular (but non-limiting) embodiments, the polymerized hydrogel is a multi-layer structure that comprises: a scrim having a first and a second side with a gel tie layer attached to the first side of the scrim, and a gel skin layer attached to the second side of the scrim. The gel tie layer is designed for contact with the transducer array, while the gel skin layer is designed for contact with the patient's skin. The gel tie and gel skin layers are both formed of any of the conductive gels described or otherwise contemplated herein, and may be formed of the same or different conductive gels. The scrim may be formed of any material that allows the composition to function in accordance with the present disclosure; in particular, the material from which the scrim is formed is typically selected to optimize conductivity and minimize resistance of the composition. A non-limiting example of a material from which the scrim can be formed is spun nylon. In certain non-limiting embodiments, the gel comprises and/or consists of at least one perforation extending through the entirety of the multi-layer structure. In certain non-limiting embodiments, the gel comprises at least one male protrusion(s) extending from a side of the gel skin layer that engaged a patient's skin.

The liquid hydrogel may have a similar formulation and/or similar structural characteristics to those described above for the polymerized hydrogel (with the exception of cross-linking of the polymer), or the liquid hydrogel may have a different formulation and/or different structural characteristics from the polymerized hydrogel. The only requirements for the liquid hydrogel are that the liquid hydrogel should be: (1) conductive; (2) hypoallergenic; and (3) have an osmolality that is substantially similar to the polymerized hydrogel (so that there is no substantial shrinking or swelling of the polymerized hydrogel in response to exposure to the liquid hydrogel). For example (but not by way of limitation), the osmolality of the liquid hydrogel may be substantially identical to an osmolality of the polymerized hydrogel or may vary therefrom by less than about 25%, or less than about 20%, or less than about 15%, or less than about 14%, or less than about 13%, or less than about 12%, or less than about 11%, or less than about 10%, or less than about 9%, or less than about 8%, or less than about 7%, or less than about 6%, or less than about 5%, or less than about 4%, or less than about 3%, or less than about 2%, or less than about 1%.

One non-limiting example of a commercially available liquid hydrogel that may be utilized in accordance with the present disclosure is CARRASYN® V hydrogel wound dressing (Medline Industries, Inc., Northfield, Ill.). This product contains aloe barbadensis leaf juice, carbomer, citric acid, disodium EDTA, glutamic acid, imidazolidinyl urea, methylparaben, panthenol, potassium sorbate, PVP, sodium benzoate, sodium chloride, sodium metabisusulfite, triethanolamine, and water. However, this hydrogel formulation is provided for illustrative purposes only. Any other hydrogel formulations that can function in the assemblies/transducer arrays as described herein also falls within the scope of the present disclosure.

In certain non-limiting embodiments, the polymerized hydrogel may be provided with a substantially uniform thickness and consistency such that the polymerized hydrogel is substantially devoid of perforations. In other non-limiting embodiments, the polymerized hydrogel may be provided with one or more types of modifications formed therein that affect the thickness of certain portions of the polymerized hydrogel.

For example (but not by way of limitation), the polymerized hydrogel may comprise one or more openings or perforations that extends from the second surface to the first surface thereof and through the polymerized hydrogel. In another non-limiting example, the polymerized hydrogel may comprise one or more recesses, indentations, or channels that extend inwardly from the second surface of the polymerized conductive hydrogel but do not extend all the way to the first surface thereof. In yet another non-limiting example, the polymerized conductive hydrogel may comprise one or more protrusions that extend outwardly from the second surface thereof. In yet another non-limiting example, the polymerized conductive hydrogel may be provided with a combination of two or more of the above modifications.

In the first two examples above (i.e., hydrogels with openings/perforations or recesses/indentations/channels), the hydrogel is provided with a base thickness that decreases in the areas of the modifications; in the third example above (i.e., hydrogels with protrusions), the hydrogel has a base thickness that increases in the areas of the protrusion(s).

The presence of openings/perforations/recesses/indentations/channels, as well as wells or voids formed between protrusions, serves at least two purposes. First, these modifications provide a reservoir in which liquid hydrogel may be disposed. Second, the modifications may alternatively be filled with air so as to allow for increased air flow between a patient's skin and the conductive gel and thereby reducing, if not eliminating, dAEs such as (but not limited to) macerations, lesions/ulcers, and dermatitis. In addition, the presence of air in one or more modifications allows for a decrease in operating temperature when a TTField is applied to the assembly containing the modified polymerized hydrogel. In addition, the presence of one or more modifications in the hydrogel can actually increase adhesion of the hydrogel to the patient's skin.

Thus, certain non-limiting embodiments of the assembly include at least a portion of the liquid hydrogel disposed in at least one modification (i.e., perforation, recess, indentation, channel, or void/well formed between protrusions) in the polymerized hydrogel.

In certain particular (but non-limiting) embodiments, the polymerized hydrogel comprises a plurality of modifications (i.e., two or more perforations, recesses, indentations, channels, or voids/wells formed between protrusions), and at least a portion of the plurality of modifications have liquid hydrogel disposed therein. For example (but not by way of limitation), liquid hydrogel may be disposed in at least about 1% of the modifications, at least about 5% of the modifications, at least about 10% of the modifications, at least about 15% of the modifications, at least about 20% of the modifications, at least about 25% of the modifications, at least about 30% of the modifications, at least about 35% of the modifications, at least about 40% of the modifications, at least about 45% of the modifications, at least about 50% of the modifications, at least about 55% of the modifications, at least about 60% of the modifications, at least about 65% of the modifications, at least about 70% of the modifications, at least about 75% of the modifications, at least about 80% of the modifications, at least about 85% of the modifications, at least about 90% of the modifications, at least about 95% of the modifications, or at least about 100% of the modifications as well as any percent value falling between two of the above values. In addition, the liquid hydrogel may be disposed in a percentage of modifications in a range formed of any of the values listed above (i.e., a range of from about 5% to about 50% of the modifications, a range of from about 10% to about 40% of the modifications, a range of from about 15% to about 35% of the modifications, etc.), or a range formed of any two values that fall between two of the above values.

In a particular (but non-limiting) embodiment, all of the modifications may have liquid hydrogel disposed therein. In another particular (but non-limiting) embodiment, a portion of the modifications may have liquid hydrogel disposed therein, while another portion of the modifications may be substantially devoid of liquid hydrogel. For example (but not by way of limitation), at least about 1% of the modifications may be substantially devoid of liquid hydrogel, such as (but not limited to), at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more of the modifications, as well as any percent value falling between two of the above values. In addition, the percentage of modifications that are substantially devoid of liquid hydrogel may fall within a range formed of any of the values listed above (i.e., a range of from about 5% to about 50%, a range of from about 10% to about 40%, a range of from about 15% to about 35%, etc.), or a range formed of any two values that fall between two of the above values.

In addition, when one or more modifications are present in the polymerized hydrogel, at least a portion or all of the modifications may have at least one dermatological therapeutic agent disposed therein. Any type of dermatological therapeutic agent known in the art that may enhance the hydrogel/skin interface, enhance skin conductivity, enhance adhesiveness, and/or reduce or prevent the occurrence of dAEs may be utilized in accordance with the present disclosure. Non-limiting examples of dermatological therapeutic agents that fall within the scope of the present disclosure include an anti-microbial agent, an antibiotic, an anti-viral agent, an anti-fungal agent, an anti-inflammatory agent, an anesthetic, an emollient, a cleansing agent, an astringent, and combinations thereof.

When the polymerized hydrogel comprises a plurality of modifications, the dermatological therapeutic agent may be disposed in any number of the modifications that allows the polymerized hydrogel to function in accordance with the present disclosure. For example (but not by way of limitation), the dermatological therapeutic agent may be disposed in at least about 1% of the modifications, at least about 5% of the modifications, at least about 10% of the modifications, at least about 15% of the modifications, at least about 20% of the modifications, at least about 25% of the modifications, at least about 30% of the modifications, at least about 35% of the modifications, at least about 40% of the modifications, at least about 45% of the modifications, at least about 50% of the modifications, at least about 55% of the modifications, at least about 60% of the modifications, at least about 65% of the modifications, at least about 70% of the modifications, at least about 75% of the modifications, at least about 80% of the modifications, at least about 85% of the modifications, at least about 90% of the modifications, at least about 95% of the modifications, or at least about 100% of the modifications as well as any percent value falling between two of the above values. In addition, the dermatological therapeutic agent may be disposed in a percentage of modifications in a range formed of any of the values listed above (i.e., a range of from about 5% to about 50% of the modifications, a range of from about 10% to about 40% of the modifications, a range of from about 15% to about 35% of the modifications, etc.), or a range formed of any two values that fall between two of the above values.

In addition, when the dermatological therapeutic agent is present, the dermatological therapeutic agent may be disposed within the same modifications as the liquid hydrogel, or different modifications than the liquid hydrogel. Alternatively, the presence of the dermatological therapeutic agent and liquid hydrogel may overlap in certain modifications and not overlap in others (i.e., certain modifications may include both therapeutic agent and liquid hydrogel, while other modifications may include one substance but not the other; also, yet other modifications may be present that include neither agent or liquid hydrogel).

In certain other non-limiting embodiments, the assembly comprises at least one of any of the electrodes described herein above in combination with a polymerized conductive hydrogel similar to that described herein, except that the polymerized conductive hydrogel has at least one compartment extending from the second surface thereof, and wherein the at least one compartment contains a liquid conductive hydrogel disposed therein (wherein the liquid conductive hydrogel may be any of those described or otherwise contemplated herein). In addition, at least a portion of the at least one compartment is formed of a material that allows release of the liquid conductive hydrogel therefrom, such as (but not limited to), in response to application of an amount of pressure thereto and/or released over time (i.e., a controlled release-type material).

For example (but not by way of limitation), the material from which the at least one compartment is formed may have one or more pores therein that allows release of the liquid conductive hydrogel in response to pressure and/or time. Alternatively, the material from which the at least one compartment is formed may be devoid of pores.

When a plurality of liquid hydrogel-containing compartments is present, the thicknesses of the material from which two or more of the compartments are formed may be the same, such that the liquid hydrogel is released from both at substantially the same time/rate. Alternatively, two or more of the liquid hydrogel-containing compartments may be formed of different materials and/or different thicknesses of material so as to allow release of the liquid conductive hydrogel at different amounts of pressure or time.

In certain non-limiting embodiments, the assembly further includes a liner disposed on at least a portion of the second surface of the polymerized hydrogel and the at least one compartment.

In certain non-limiting embodiments, the polymerized conductive gel having the liquid hydrogel-containing compartments thereon may further include at least one of any of the modifications that extends inwardly or outwardly from the second surface thereof, as described in detail herein above.

In certain non-limiting embodiments, this assembly containing the liquid hydrogel-containing compartments on the polymerized conductive gel may further include at least one of any of the dermatological therapeutic agents disclosed or otherwise contemplated herein. The dermatological therapeutic agent(s) may be disposed on a portion of the second surface of the polymerized conductive hydrogel, and/or the dermatological therapeutic agent(s) may be disposed within the at least one compartment containing the liquid conductive hydrogel. In yet another alternative, the assembly may include at least two compartments, wherein one or more compartments contains the liquid conductive hydrogel, and one or more other compartments contains the dermatological therapeutic agent(s); in addition, in a particular (but non-limiting) embodiment, one or more compartments containing both liquid conductive hydrogel and dermatological therapeutic agent(s) may also be present.

Certain non-limiting embodiments of the present disclosure are related to transducer arrays that include one or more of any of the assemblies disclosed or otherwise contemplated herein. For example (but not by way of limitation), the transducer array may include at least about one assembly, at least about two assemblies, at least about three assemblies, at least about four assemblies, at least about five assemblies, at least about six assemblies, at least about seven assemblies, at least about eight assemblies, at least about nine assemblies, at least about 10 assemblies, at least about 11 assemblies, at least about 12 assemblies, at least about 13 assemblies, at least about 14 assemblies, at least about 15 assemblies, at least about 16 assemblies, at least about 17 assemblies, at least about 18 assemblies, at least about 19 assemblies, at least about 20 assemblies, at least about 21 assemblies, at least about 22 assemblies, at least about 23 assemblies, at least about 24 assemblies, at least about 25 assemblies, at least about 26 assemblies, at least about 27 assemblies, at least about 28 assemblies, at least about 29 assemblies, at least about 30 assemblies, at least about 35 assemblies, at least about 40 assemblies, at least about 45 assemblies, at least about 50 assemblies, at least about 55 assemblies, at least about 60 assemblies, at least about 65 assemblies, at least about 70 assemblies, at least about 75 assemblies, at least about 80 assemblies, at least about 85 assemblies, at least about 90 assemblies, at least about 95 assemblies, at least about 100 assemblies, or more, as well as a range of any of the above values (i.e., a range of from about 2 assemblies to about 30 assemblies, a range of from about 9 assemblies to about 20 assemblies, etc.), or a range formed of any two values that fall between two of the above values.

In certain particular (but non-limiting) embodiments, pairs of transducer arrays cooperate in a TTField-generating system to generate an alternating electric field having a frequency in a range of from about 50 kHz to about 500 kHz upon application to a patient's skin in combination with the polymerized and liquid hydrogels. Examples of transducer arrays that function as part of a TTField system are known in the art and are described, for example but not by way of limitation, in U.S. Pat. Nos. 7,016,725; 7,089,054; 7,333,852; 7,565,205; 8,244,345; 8,715,203; 8,764,675; 10,188,851; and 10,441,776; and in US Patent Application Nos. US 2018/0160933; US 2019/0117956; US 2019/0307781; and US 2019/0308016. Therefore, no further description thereof is deemed necessary.

Certain non-limiting embodiments of the present disclosure are related to kits that include any of the components of the TTField generating systems and/or any of the assemblies disclosed or otherwise contemplated herein. For example (but not by way of limitation), the kit may include any of the polymerized conductive hydrogels disclosed or otherwise contemplated herein along with any of the liquid conductive hydrogels disclosed or otherwise contemplated herein. Alternatively (and/or in addition thereto), the kit may contain one or more assemblies that includes at least one electrode in combination with the polymerized conductive hydrogel(s) and the liquid conductive hydrogel(s).

In a particular (but non-limiting) embodiment, the kit may further include instructions for applying at least a portion of the liquid hydrogel to at least a portion of the polymerized hydrogel (and potentially applying this assembly to a patient's skin), and/or for applying the polymerized hydrogel having liquid hydrogel-containing compartments extending therefrom to a patient's skin, and/or for applying the assembly to a patient's skin.

In certain non-limiting embodiments, the polymerized conductive hydrogel is for application to a patient's skin and for placement between the patient's skin and at least one transducer array that generates an alternating electric field having a frequency in a range of from about 50 kHz to about 500 kHz; in addition, the polymerized conductive hydrogel comprises a first surface and a second surface. Also in this embodiment, the liquid conductive hydrogel is for disposal on at least a portion of the second surface of the polymerized hydrogel.

In certain non-limiting embodiments, the kit includes at least one dermatological therapeutic agent. Any type of dermatological therapeutic agent known in the art that would be useful for use in combination with the polymerized and liquid hydrogels and a transducer array/TTField-generating system may be utilized in accordance with the present disclosure. Non-limiting examples of dermatological therapeutic agents that may be utilized in accordance with the present disclosure include an anti-microbial agent, an antibiotic, an anti-viral agent, an anti-fungal agent, an anti-inflammatory agent, an anesthetic, an emollient, a cleansing agent, an astringent, and combinations thereof.

In addition, the kit may further include at least one removable liner attached to at least a portion of a surface of the polymerized hydrogel for protecting the surface until use. For example (but not by way of limitation), the polymerized hydrogel may have a removable top liner and/or a removable bottom liner attached to the first and second surfaces thereof, respectively.

In certain particular (but non-limiting) embodiments, the kit may further include at least one pair of transducer arrays that generates an alternating electric field having a frequency in a range of from about 50 kHz to about 500 kHz upon application to a patient's skin in combination with the gel composition (i.e., transducer arrays that function as part of a TTField-generating system). For example (but not by way of limitation), the kit may include at least about two pairs of transducer arrays, at least about four pairs of transducer arrays, at least about six pairs of transducer arrays, at least about eight pairs of transducer arrays, at least about ten pairs of transducer arrays, at least about 12 pairs of transducer arrays, at least about 14 pairs of transducer arrays, at least about 16 pairs of transducer arrays, at least about 18 pairs of transducer arrays, at least about 20 pairs of transducer arrays, at least about 22 pairs of transducer arrays, at least about 24 pairs of transducer arrays, at least about 26 pairs of transducer arrays, at least about 28 pairs of transducer arrays, at least about 30 pairs of transducer arrays, at least about 32 pairs of transducer arrays, at least about 34 pairs of transducer arrays, at least about 36 pairs of transducer arrays, at least about 38 pairs of transducer arrays, at least about 40 pairs of transducer arrays, at least about 42 pairs of transducer arrays, at least about 44 pairs of transducer arrays, at least about 46 pairs of transducer arrays, at least about 48 pairs of transducer arrays, at least about 50 pairs of transducer arrays, or more, as well as a range of pairs of transducer arrays that combines any two of the above-referenced values (i.e., a range of from about two pairs of transducer arrays to about 50 pairs of transducer arrays, a range of from about two pairs of transducer arrays to about 20 pairs of transducer arrays, etc.), and a range that combines two integers that fall between two of the above-referenced values (i.e., a range of from about one pair of transducer arrays to about 15 pairs of transducer arrays, etc.).

Examples of transducer arrays that function as part of a TTField system are known in the art and are described, for example but not by way of limitation, in U.S. Pat. Nos. 7,016,725; 7,089,054; 7,333,852; 7,565,205; 8,244,345; 8,715,203; 8,764,675; 10,188,851; and 10,441,776; and in US Patent Application Nos. US 2018/0160933; US 2019/0117956; US 2019/0307781; and US 2019/0308016. Therefore, no further description thereof is deemed necessary.

The polymerized hydrogel may be present in the kit in any form that allows the kit to perform in accordance with the present disclosure. For example, but not by way of limitation, the polymerized hydrogel may be provided in the form of one or more sheets or one or more rolls. In addition, the polymerized hydrogel may be provided in a single, individual unit/amount, or multiple units/amounts of the polymerized hydrogel may be provided within the kit.

Likewise, the liquid hydrogel may be present in the kit in any form that allows the kit to perform in accordance with the present disclosure. For example, but not by way of limitation, the liquid hydrogel may be provided in a tube or in single use aliquots/ampules.

When one or more transducer arrays are present in the kit, two or more components of the kit may be assembled for use thereof. For example (but not by way of limitation), the polymerized hydrogel may be disposed upon the surface of the electrodes of the transducer arrays and this combination sealed together (either with or without a removable liner disposed upon the polymerized hydrogel) prior to placement of the combination within the kit (which would also contain a separate container(s) of liquid hydrogel). In another example, both the polymerized hydrogel and the liquid hydrogel may be disposed upon the surface of the electrodes of the transducer arrays and this entire combination sealed together (either with or without a removable liner disposed upon the hydrogels) prior to placement of the combination within the kit.

In addition to the components described in detail herein above, the kits may further contain other component(s)/reagent(s) for performing any of the particular methods described or otherwise contemplated herein. For example (but not by way of limitation), the kits may additionally include: (i) components for preparing the skin prior to disposal of the two hydrogel compositions and transducer arrays thereon (i.e., a razor, a cleansing composition or wipe/towel, etc.); (ii) components for removal of the gel/transducer array(s); and/or (iii) components for cleansing of the skin after removal of the gel/transducer array(s). The nature of these additional component(s)/reagent(s) will depend upon the particular treatment format and/or area/organ to be treated, and identification thereof is well within the skill of one of ordinary skill in the art; therefore, no further description thereof is deemed necessary. Also, the components/reagents present in the kits may each be in separate containers/compartments, or various components/reagents can be combined in one or more containers/compartments, depending on the sterility, cross-reactivity, and stability of the components/reagents.

The kit may be disposed in any packaging that allows the components present therein to function in accordance with the present disclosure. In certain non-limiting embodiments, the kit further comprises a sealed packaging in which the polymerized conductive hydrogel(s) and the liquid conductive hydrogel(s) (and/or the one or more assemblies) are disposed. In certain particular (but non-limiting) embodiments, the sealed packaging is substantially impermeable to air (so as to allow the hydrogels to substantially maintain their water content) and/or substantially impermeable to light (as certain components may be light sensitive).

In addition, the kit can further include a set of written instructions explaining how to use one or more components of the kit. A kit of this nature can be used in any of the methods described or otherwise contemplated herein.

In certain non-limiting embodiments, the kit has a shelf life of at least about six months, such as (but not limited to), at least about nine months, or at least about 12 months.

Certain non-limiting embodiments of the present disclosure are directed to a method that includes: (1) applying any of the assemblies or transducer arrays (or components of kits) disclosed or otherwise contemplated herein to a skin of a patient; and (2) generating an electric field for a period of time. In certain particular (but non-limiting) embodiments, the electric field is an alternating electric field having a frequency in a range of from about 50 kHz to about 500 kHz for a period of time.

In certain particular (but non-limiting) embodiments, step (1) includes the application of at least two pairs of transducer arrays, each along with polymerized hydrogel and liquid hydrogel disposed upon the electrodes thereof, to the patient's skin.

In certain particular (but non-limiting) embodiments, the electric field is generated within a target region of the patient. The target region typically comprises at least one tumor, and the generation of the alternating electric field selectively destroys or inhibits growth of the tumor. The alternating electric field may be generated at any frequency that selectively destroys or inhibits growth of the tumor. For example (but not by way of limitation), the alternating electric field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 400 kHz, about 425 kHz, about 450 kHz, about 475 kHz, or about 500 kHz, as well as a range formed from any of the above values (i.e., a range of from about 100 kHz to about 300 kHz, a range of from about 100 kHz to about 150 kHz, a range of from about 150 kHz to about 300 kHz, etc.), and a range that combines two integers that fall between two of the above-referenced values (i.e., a range of from about 32 kHz to about 333 kHz, a range of from about 78 kHz to about 298 kHz, etc.).

In certain particular (but non-limiting) embodiments, the alternating electric field may be generated at two or more different frequencies. When two or more frequencies are present, each frequency is selected from any of the above-referenced values, or a range formed from any of the above-referenced values, or a range that combines two integers that fall between two of the above-referenced values.

In certain particular (but non-limiting) embodiments, the assembly/transducer array is maintained upon the patient's skin for at least about three days.

In certain particular (but non-limiting) embodiments, the method includes the steps of: (3) removing the assembly/transducer array from the patient's skin; (4) preparing the patient's skin for another treatment (such as, but not limited to, cleansing of the skin and shaving of the skin, if necessary); and (5) repeating steps (1)-(2). In addition, this cycle of steps (1)-(5) can be repeated as many times as necessary.

When steps (1)-(2) are repeated, the electrodes (in combination with the hydrogels) may be placed in different positions than their original placement; relocation of the arrays in this manner further minimizes any dAEs that may occur.

One of the many advantages to the use of liquid hydrogel as disclosed herein, either alone or in combination with perforations/modifications in the polymerized hydrogel, is a reduction in maceration of the skin due to prolonged exposure to the hydrogel; reduction in the maceration of the contacted skin thereby also reduces the skin's susceptibility to infection, given the reduction in the presence of lesions/ulcers resulting from the maceration. This feature can be further enhanced by the addition of one or more dermatological therapeutic agents (such as, but not limited to, an anti-microbial agent, an antibiotic, an anti-viral agent, an anti-fungal agent, an emollient, etc.) to the system, as described elsewhere herein. In addition, the use of perforated/modified polymerized hydrogel containing liquid hydrogel in only a portion of the perforations/modifications will allow for increased air flow between a patient's skin and the conductive gel, thereby allowing for a reduced operating temperature and providing a cooling effect to the patient's skin, which further decreases the risk of maceration of the skin.

Another advantage of the presence of liquid hydrogel, either alone or in combination with perforations in the polymerized hydrogel, is the reduction in both skin lift-off and conductivity loss observed over time in response to hair growth. As stated above, a patient's skin is typically shaved prior to disposal of the TTField-generating system thereon; however, hair growth over time will subsequently cause the hydrogel-electrode assembly to lift off the skin, thereby reducing the conductivity of the system. The presence of liquid hydrogel will provide a greater "cushioning" effect and not impede hair growth to the same extent as a semi-solid polymerized hydrogel. In addition, the presence of perforations/recesses/indentations will provide receptacle(s) that can receive the new hair growth, thereby further reducing any skin lift-off. Further, the liquid hydrogel in the perforations/recesses/indentations allows current to flow into the hair follicle; in this manner, conductivity is actually increased while also providing a mechanism by which tissues beneath the dermis can be accessed.

Referring now to the Figures, shown therein are non-limiting embodiments of various components and configurations of the assemblies disclosed herein, along with transducer arrays and TTField-generating systems containing same. While hydrogels are specifically shown in the Figures, a person having ordinary skill in the art should readily understand that the various configurations disclosed herein may be utilized with any conductive gel commonly known in the art, as well as that the liquid gels disclosed herein may be any conductive liquid gel known in the art or otherwise contemplated herein.

FIG. 1 is a schematic representation of a portion of an existing TTField-generating system that can be utilized in accordance with the present disclosure. As generally shown in FIG. 1, a conductive gel provides an adhesion interface between at least one insulated electrode of the TTField-generating system and a patient's epidermal layer for delivery of at least one TTField to and/or through the patient's epidermal and/or dermal/subcutaneous layers.

Figure 2:
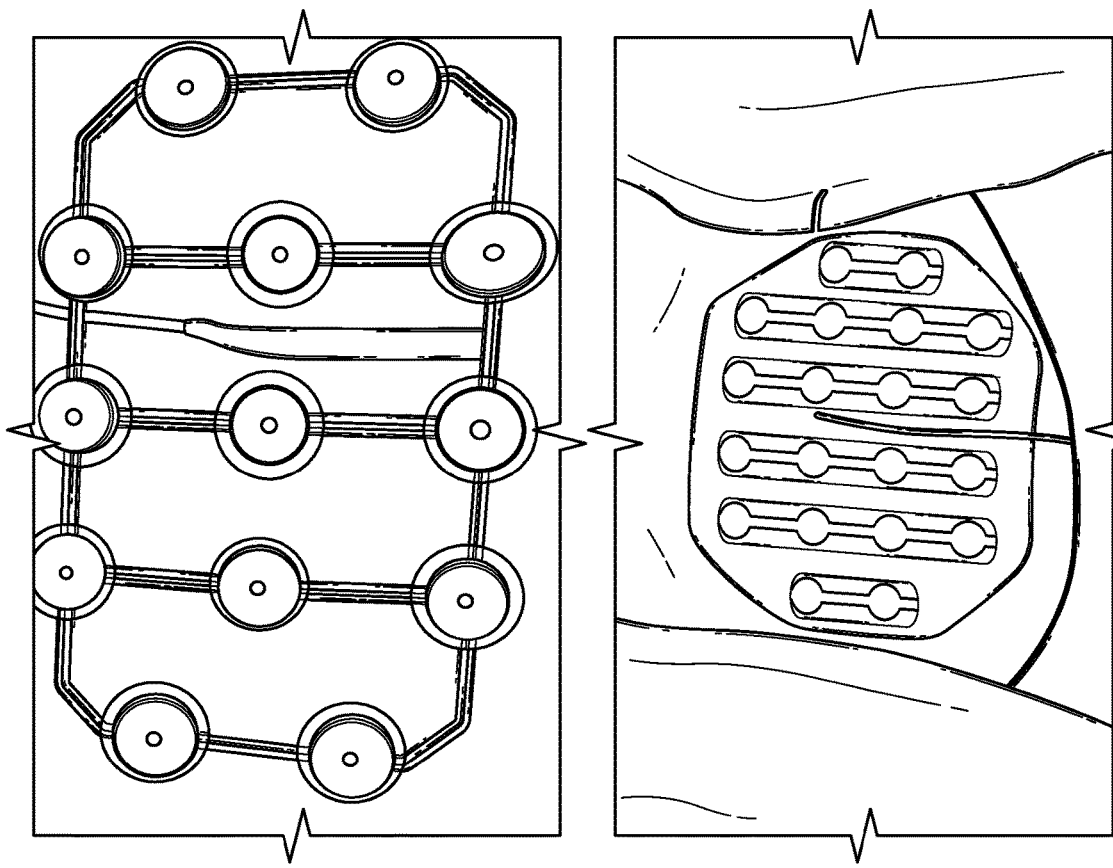
FIG. 2 is a representation of two existing transducer arrays for use in a TTField-generating system, wherein the transducer array in the upper panel includes 13 electrode-conductive gel assemblies, and wherein the transducer array in the lower panel includes 20 electrode-conductive gel assemblies and has been disposed upon a patient's skin.

FIG. 2 depicts two existing transducer arrays for use in a TTField-generating system. As can be seen, each of these arrays includes a plurality of the electrode-gel assemblies shown in FIG. 1. The array in the upper panel contains 13 electrodes, while the array in the lower panel contains 20 electrodes; in addition, the lower panel depicts attachment of the array to a patient's skin.

Figure 3:
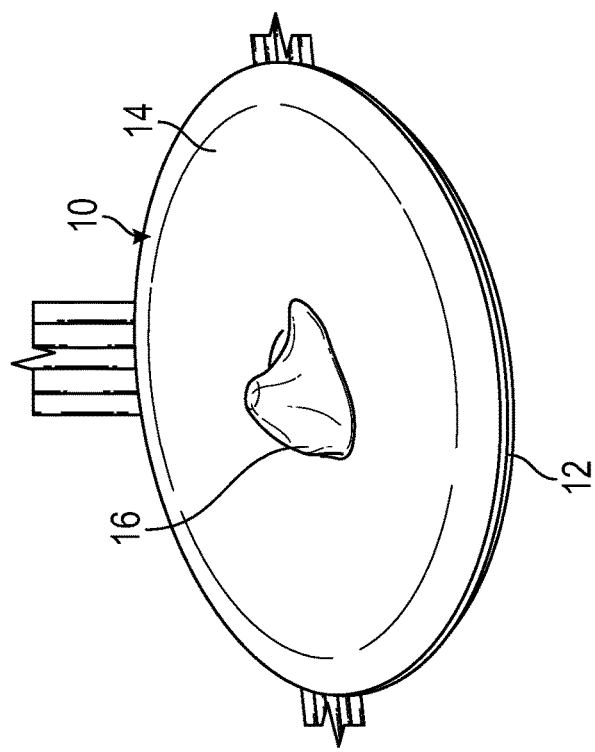
FIG. 3 shows one non-limiting embodiment of an assembly constructed in accordance with the present disclosure, wherein the assembly includes an electrode, a polymerized conductive gel, and a liquid conductive gel.

FIG. 3 illustrates an assembly 10 constructed in accordance with the present disclosure. The assembly 10 includes an electrode 12 having a polymerized conductive hydrogel layer 14 disposed thereon. Then a drop of liquid hydrogel 16 is disposed upon the polymerized hydrogel layer 14.

The amount of liquid hydrogel 16 deposited on the polymerized hydrogel layer 14 may vary, and may simply be sufficient to cover only a portion of the polymerized hydrogel layer 14; alternatively, the volume of liquid hydrogel 16 may be substantial enough to extend beyond the polymerized hydrogel layer 14 when the assembly 10 is pressed onto the surface of a patient's skin.

As shown in FIG. 3, the liquid hydrogel 16 may simply be deposited upon an existing surface of the polymerized hydrogel layer 14, and this may be accomplished by any manner known in the art. Alternatively, the polymerized hydrogel layer may be provided with one or more types of modifications, and the liquid hydrogel layer may be deposited/disposed within or in between one or more of these modifications. Various non-limiting examples of modifications to the polymerized hydrogel layer that may be utilized in accordance with the present disclosure will now be described with respect to the remaining Figures.

The electrodes utilized as part of the assemblies and transducers described herein (such as, but not limited to, the electrode 12) may be constructed in any manner and contain any components necessary to allow the assemblies and transducer arrays to function in accordance with the present disclosure. Certain non-limiting structural embodiments of electrodes are described herein after; however, these structures are provided for illustrative, exemplary purposes only, and should not be construed as limiting to the electrode structure of any of the assemblies of the present disclosure.

Figure 4A:
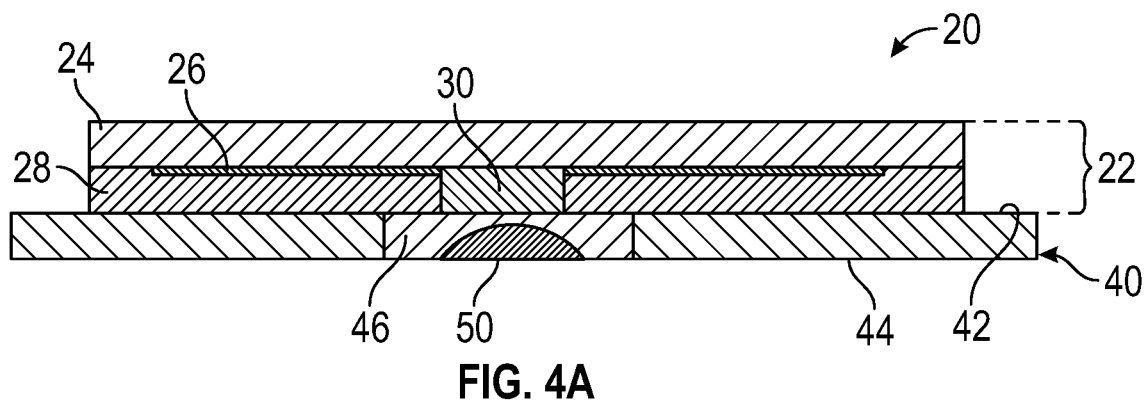
FIG. 4A is a cross-sectional view of another non-limiting embodiment of an assembly constructed in accordance with the present disclosure, wherein the polymerized conductive gel comprises a perforation extending therethrough.
Figure 4B:
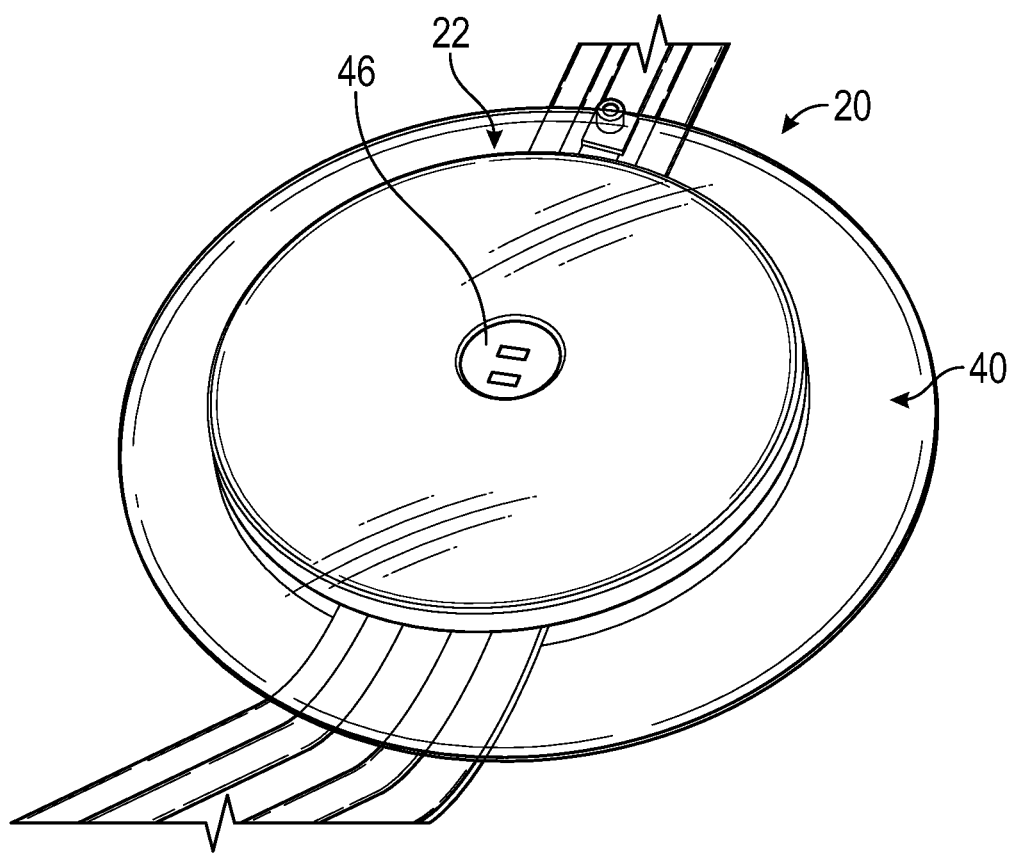
FIG. 4B is a representation of the assembly of FIG. 4A.

FIG. 4A shows a cross-sectional view of one non-limiting embodiment of an assembly 20 that is constructed in accordance with the present disclosure, while FIG. 4B contains a representation of said assembly 20. As shown in FIG. 4A, the assembly 20 comprises at least one insulated electrode 22 and a polymerized hydrogel layer 40 that is perforated. The at least one insulated electrode 22 comprises at least one non-conducting layer 24, at least one conducting layer 26, and a high capacitance layer 28 having at least one optional opening 30 disposed at least partially therethrough. As shown in FIG. 4A, the perforated hydrogel layer 40 comprises a first surface 42 and a second surface 44 wherein a single, central perforation 46 extends from the second surface 44 to the first surface 42 thereof and thus through the polymerized hydrogel layer 40. Then a quantity of liquid hydrogel 50 is deposited/disposed within at least a portion of the perforation 46.

In one non-limiting embodiment, the at least one conducting layer 26 comprises and/or consists of at least one conducting element and/or compound, including, by way of example only, elemental silver. In one non-limiting embodiment, the high capacitance layer 28 comprises and/or consists of ceramic, and the optional opening 30 contains and/or is coated (for instance, an inner perimeter of the optional opening 30 is coated) with at least one epoxy and/or at least one temperature sensor.

The perforated polymerized hydrogel layer 40 may comprise any polymerizable conductive gel(s) as set forth in greater detail elsewhere herein. While shown in FIGS. 4A-4B as comprising a single, central perforation extending through the polymerized hydrogel layer 40, a person having ordinary skill in the art should readily appreciate that the polymerized hydrogel layer 40 may comprise any number of perforations extending through the polymerized hydrogel layer 40 capable of accomplishing the present disclosure. Non-limiting examples include about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, 55, about 60, about 65, about 70, about 75, about 80, about 85, about 90, about 95, about 100, about 125, about 150, about 175, about 200, about 225, about 250, about 275, about 300, about 325, about 350, about 375, about 400, about 425, about 450, about 500, about 525, about 550, about 575, about 600, about 625, about 650, about 675, about 700, about 725, about 750, about 775, about 800, about 825, about 850, about 875, about 900, about 925, about 950, about 975, or greater than or equal to about 1,000 perforations, as well as a range that combines any two of the above-referenced values (i.e., a range of from about one perforation to about 500 perforations, a range of from about 10 perforations to about 100 perforations, etc.), and a range that combines two integers that fall between two of the above-referenced values (i.e., a range of from about 22 perforations to about 63 perforations, etc.).

In addition, while shown in FIGS. 4A-4B (as well as FIGS. 5A-5D) as being substantially circular in shape, a person having ordinary skill in the art should readily understand that the perforation(s) may be any shape capable of accomplishing the present disclosure, including, but not limited to, circular, triangular, square, rectangular, pentagonal, hexagonal, heptagonal, octagonal, nonagonal, decagonal, hendecagonal, dodecagonal, or any shape that is substantially similar to one of the above shapes, or any shape with any number of sides capable of accomplishing the present disclosure.

The perforation(s) may be of any dimension capable of accomplishing the present disclosure. For example, but not by way of limitation, a perforation may have a dimension in which the distance across a particular perforation is about 0.1 millimeter, about 0.2 millimeter, about 0.3 millimeter, about 0.4 millimeter, about 0.5 millimeter, about 0.6 millimeter, about 0.7 millimeter, about 0.8 millimeter, about 0.9 millimeter, about 1.0 millimeter, about 1.1 millimeter, about 1.2 millimeter, about 1.3 millimeter, about 1.4 millimeter, about 1.5 millimeter, about 1.6 millimeter, about 1.7 millimeter, about 1.8 millimeter, about 1.9 millimeter, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, or greater than or equal to about 3.5 millimeters, or a dimension that falls within a range of two of the above values (i.e., a dimension in a range of from about 0.1 mm to about 3.5 mm, a range of from about 0.5 mm to about 2 mm, etc.), or a range that combines two integers that fall between two of the above-referenced values (i.e., a range of from about 1.05 mm to about 2.95 mm, etc.).

When the perforated hydrogel layer 40 comprises more than one perforation, the perforations may have the same or different dimension(s), as well as the same or different shapes.

The perforation(s) may be formed in and through the polymerized hydrogel layer 40 via any technique capable of accomplishing the present disclosure, including, but not limited to, via dye-cutting techniques and/or laser-cutting techniques. The formation of the perforations in and through the polymerized hydrogel layer 40 may be accomplished via automated or non-automated process(es).

In the non-limiting embodiment shown in FIGS. 4A-4B, about 90% of the polymerized hydrogel layer 40 does not contain the perforation/opening 46 and thus adheres to the patient's epidermal layer, while the single, central perforation 46 comprises about 10% of the polymerized hydrogel layer 40. In the absence of the liquid hydrogel 50, a first test (shown in Table 1A) demonstrated that the above-described polymerized hydrogel layer 40 comprising the single, central perforation 46 introduces air under the high capacitance layer 28 via the single, central perforation 46 which results in a 60% increase in conductivity as compared to an exemplary non-perforated hydrogel, as well as a reduction in operating temperature from 40° C. to 37.2° C. In addition, as shown below in Table 1B, a second test demonstrated that the above-described polymerized hydrogel layer 40 comprising the single, central perforation 46 introduces air under the high capacitance layer 28 via the single, central perforation 46, which results in a 105% increase in conductivity as compared to an exemplary non-perforated hydrogel, as well as a reduction in operating temperature from 39.6° C. to 38.1° C.

TABLE 1A

Comparison of Non-Perforated Hydrogel and Single Perforated Hydrogel

| Parameter | Non-Perforated Hydrogel | Perforated Hydrogel Shown in FIGS. 4A-4B |
| --- | --- | --- |
| Conductance (Current) | 1950 mA | 3136 mA |
| Voltage | 75 V | 100 V |

TABLE 1A-continued

Comparison of Non-Perforated Hydrogel and Single Perforated Hydrogel

| Parameter | Non-Perforated Hydrogel | Perforated Hydrogel Shown in FIGS. 4A-4B |
| --- | --- | --- |
| Resistance | 38 ohms | 31 ohms |
| Operating Temperature (Max) | 40° C. | 37.2° C. |
| % Increase in Conductance | (1950 mA − 3136 mA)/ 1950 mA = ~60.82% Increase | |

TABLE 1B

Comparison of Non-Perforated Hydrogel and Single Perforated Hydrogel

| Parameter | Non-Perforated Hydrogel | Perforated Hydrogel Shown in FIGS. 4A-4B |
| --- | --- | --- |
| Conductance (Current) | 1554 mA | 3197 mA |
| Voltage | 59 V | 101 V |
| Resistance | 37 ohms | 31 ohms |
| Operating Temperature (Max) | 39.6° C. | 38.1° C. |
| % Increase in Conductance | (1554 mA − 3197 mA)/ 1554 mA = ~105.73% Increase | |

Figure 5A:
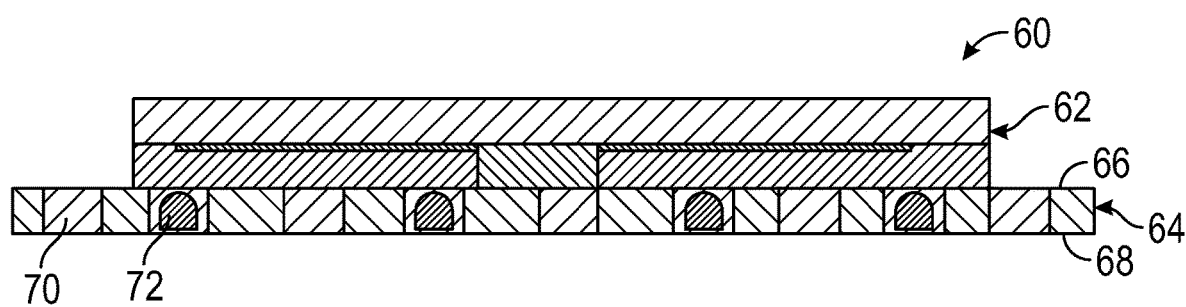
FIG. 5A is a cross-sectional view of another non-limiting embodiment of an assembly constructed in accordance with the present disclosure, wherein the polymerized conductive gel comprises a plurality of perforations extending therethrough.
Figure 5B:
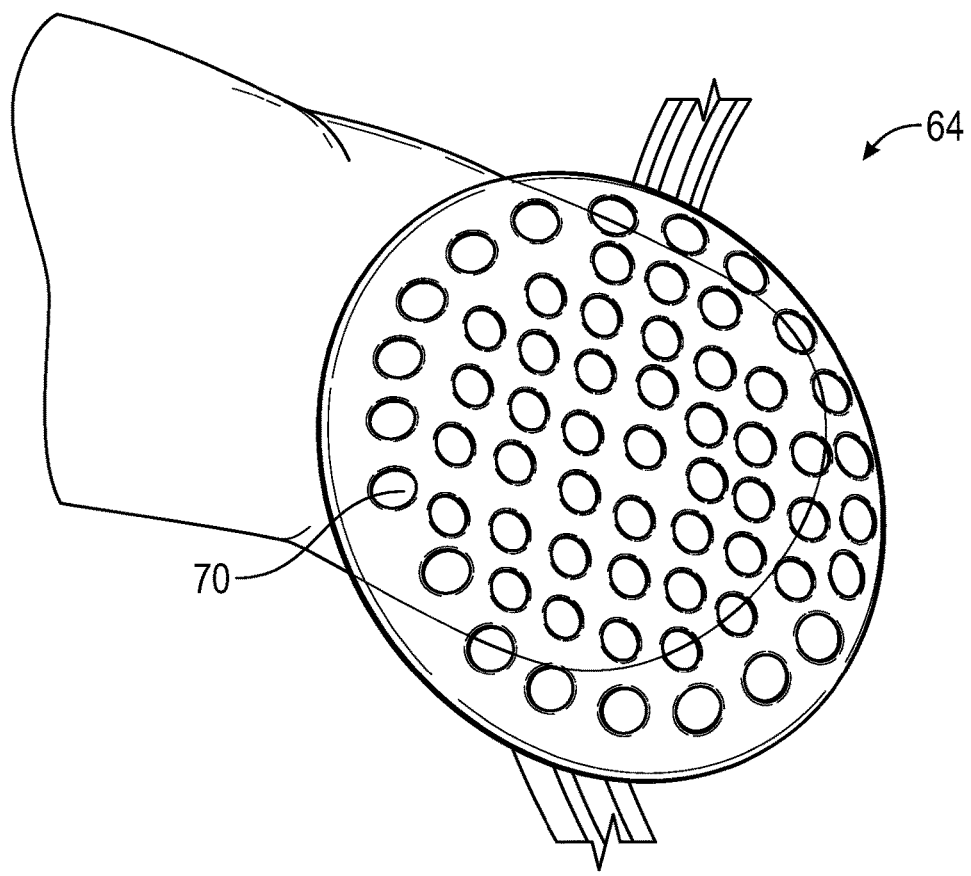
FIG. 5B contains a representation of the perforated polymerized gel layer of the assembly of FIG. 5A.
Figure 5C:
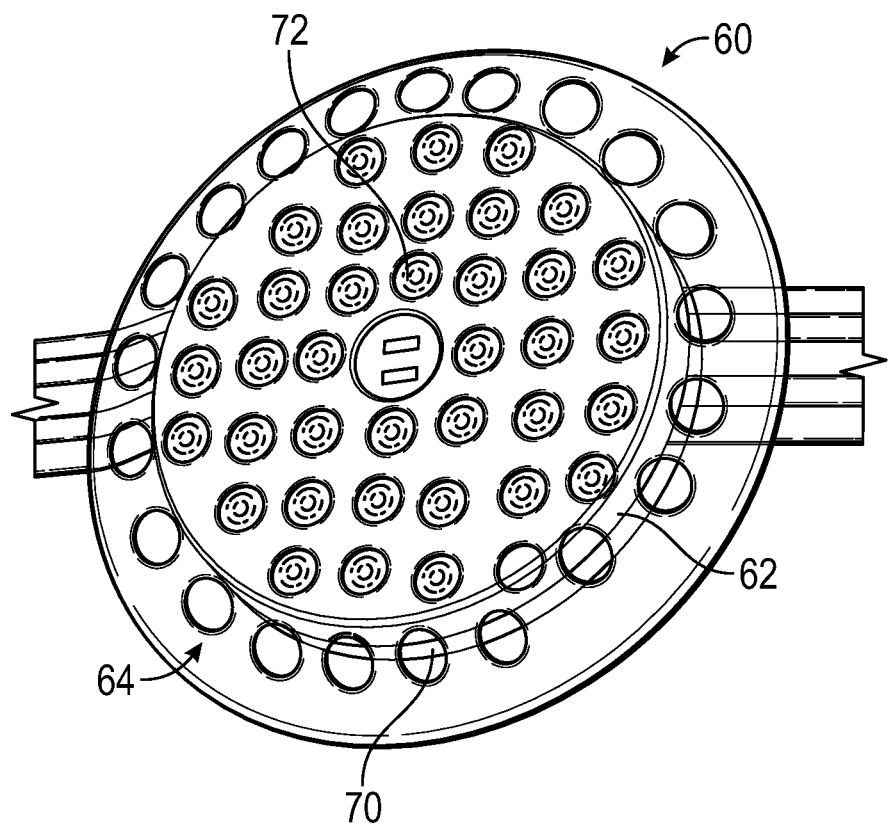
FIG. 5C contains a representation of the assembly of FIG. 5A, wherein a portion of the perforations of the polymerized hydrogel layer have liquid hydrogel disposed therein.

Referring now to FIGS. 5A-5C, shown therein is another non-limiting embodiment of an assembly 60 for a TTField-generating system that is constructed in accordance with the present disclosure. The assembly 60 is similar to the assembly 20 and includes an insulated electrode 62 identical to the electrode 22. The assembly 60 further includes a polymerized hydrogel layer 64 that comprises a first surface 66 and a second surface 68 wherein multiple perforations 70 extend from the second surface 68 to the first surface 66 through the polymerized hydrogel layer 64. Then a quantity of liquid hydrogel 72 is deposited/disposed within at least a portion of at least one of the perforations 70.

In the non-limiting embodiment shown in FIGS. 5A-5C, about 50% of the polymerized hydrogel layer 64 does not contain perforations and thus adheres to the patient's epidermal layer, while the multiple perforations 70 comprise about 50% of the polymerized hydrogel layer 64. In the absence of liquid hydrogel, and as can be seen below in Table 2, the increased introduction of air under the high capacitance layer of the electrode 62 via the multiple perforations 70 within the polymerized hydrogel layer 64 results in a 14% increase in conductance as compared to an exemplary non-perforated hydrogel, as well as a reduction in operating temperature from 36.6° C. to 34° C.

TABLE 2

Comparison of Non-Perforated Hydrogel and Hydrogel with Multiple Perforations

| Parameter | Non-Perforated Hydrogel | Perforated Hydrogel Shown in FIGS. 5A-5B |
| --- | --- | --- |
| Conductance (Current) | 2312 mA | 2642 mA |
| Voltage | 107 V | 93 V |

TABLE 2-continued

Comparison of Non-Perforated Hydrogel
and Hydrogel with Multiple Perforations

| Parameter | Non-Perforated Hydrogel | Perforated Hydrogel Shown in FIGS. 5A-5B |
|---|---|---|
| Resistance | 46 ohms | 35 ohms |
| Operating Temperature (Max) | 36.6° C. | 34.0° C. |
| % Increase in Conductance | (2312 mA − 2642 mA)/ 2312 mA = ~14.27% Increase | |

FIG. 5B contains a representation of the perforated hydrogel layer 64 visualizing the perforations 70 that extend from the second surface 68 to the first surface 66 thereof. In addition, FIG. 5C contains a representation of the assembly 60 that includes the electrode 62, the polymerized hydrogel 64 having the perforations 70 therein, and the liquid hydrogel 72 deposited/disposed within a portion of the perforations 70.

Figure 5D:
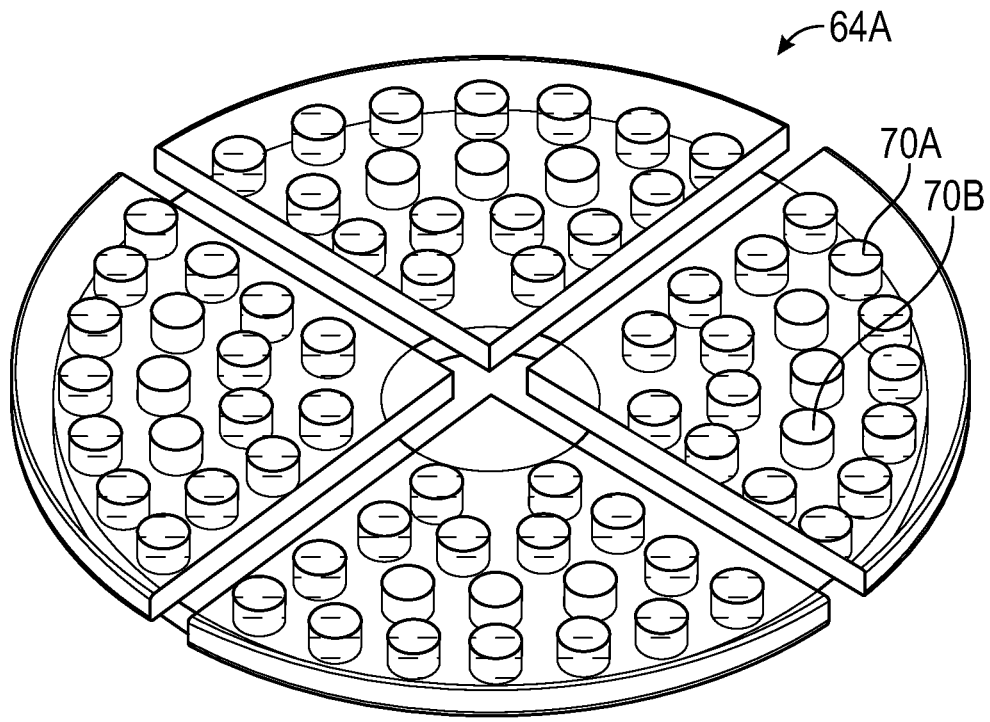
FIG. 5D is a schematic illustration of a perforated polymerized conductive gel having liquid hydrogel disposed in a portion of the perforations thereof and air disposed in the remaining perforations.

As stated herein above, when the polymerized hydrogel is provided with perforations, at least a portion (or all) of the perforations may be filled with liquid hydrogel and/or at least a portion (or all) of the perforations may be filled with air. FIG. 5D is a schematic illustration of a perforated polymerized hydrogel 64A having perforations 70A with liquid hydrogel disposed therein and perforations 70B with no liquid hydrogel (and thus only air) disposed therein. In this Figure, about 80-85% of the perforations have liquid hydrogel disposed therein; however, the amount of perforations containing liquid hydrogel can vary widely, as discussed in detail above, and therefore the particular amounts shown in the drawings is for purpose of example only.

Figure 6A:
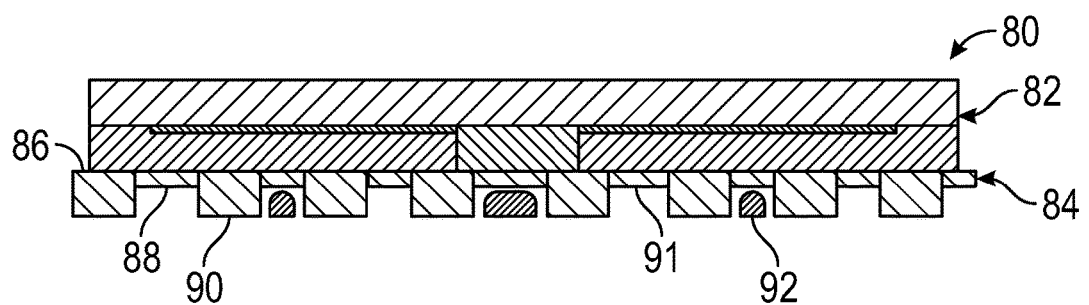
FIG. 6A is a cross-sectional view of yet another non-limiting embodiment of an assembly constructed in accordance with the present disclosure, wherein the polymerized conductive hydrogel layer comprises a plurality of protrusions extending therefrom.
Figure 6B:
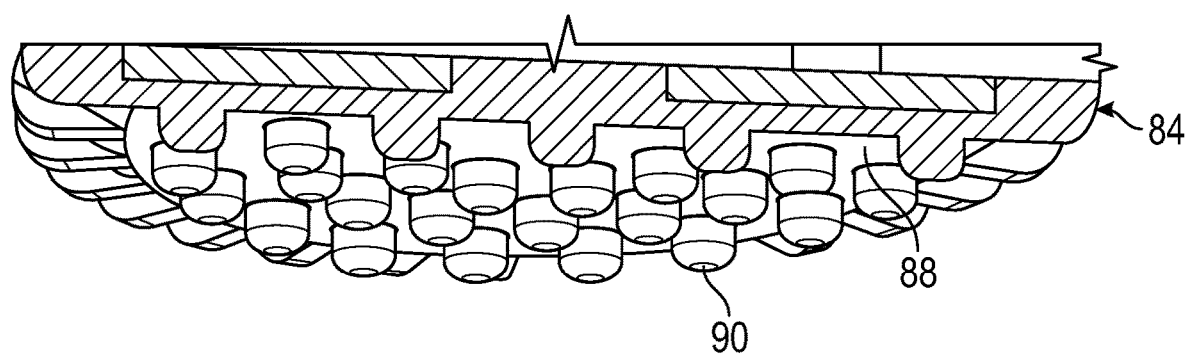
FIG. 6B is a schematic illustration of the polymerized hydrogel layer of the assembly of FIG. 6A.
Figure 8:
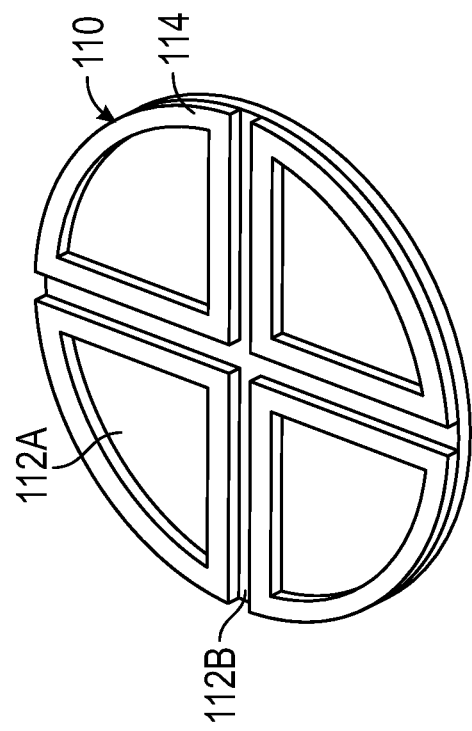
FIGS. 7, 8, 9, and 10 depict non-limiting alternative embodiments and configurations of modifications to polymerized conductive hydrogel layers constructed in accordance with the present disclosure.
Figure 10:
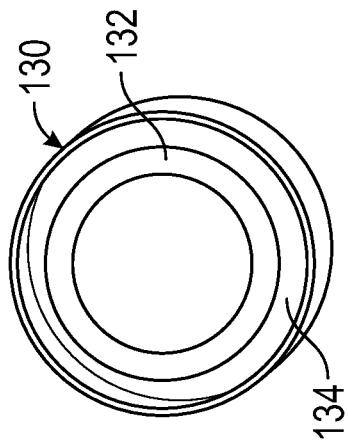
Figure 7:
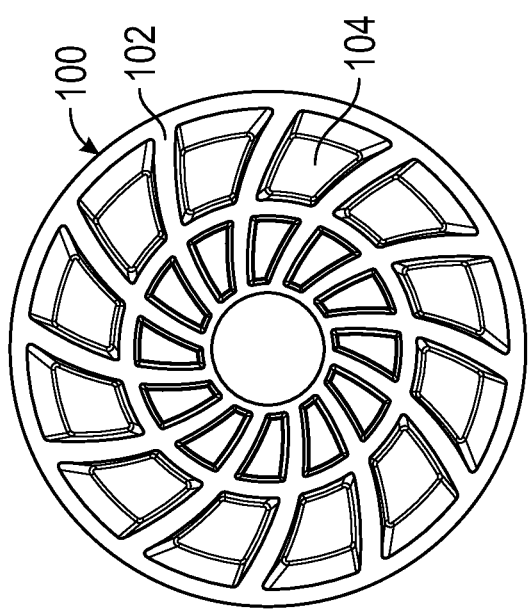
Figure 9:
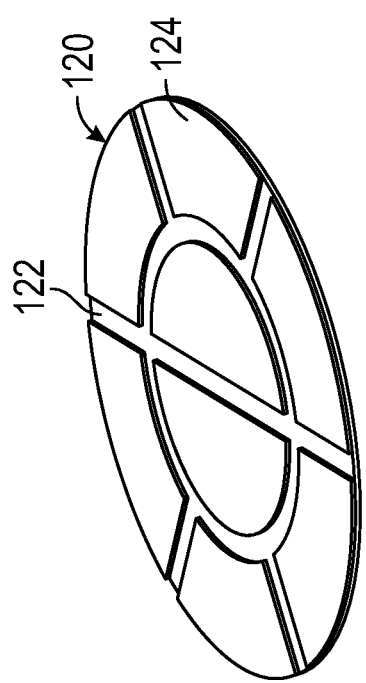

Referring now to FIGS. 6A-6B, shown therein is a cross-sectional view of yet another non-limiting embodiment of an assembly 80 for a TTField-generating system that is constructed in accordance with the present disclosure and contains at least one electrode 82 and a polymerized hydrogel 84. The electrode 82 is similar to the electrode 22 described in detail herein above with reference to FIGS. 2A-2B. Accordingly, no additional description is deemed necessary.

In this non-limiting embodiment, the polymerized hydrogel layer 84 comprises a first surface 86 that substantially adheres to the electrode 82, and a second surface 88 that has at least one protrusion 90 extending therefrom. The at least one protrusion(s) 90 engage and adhere to the patient's epidermal layer, while pockets of air are introduced as a result of the spacing between two or more of the protrusions 90. In addition, at least one well or channel 91 is formed between two or more of the protrusions 90, and at least one drop of liquid hydrogel 92 is disposed within at least a portion of the wells/channels 91.

The number of protrusion(s) 90 present on the second surface 88 of the polymerized hydrogel layer 84 may be any number of protrusions capable of accomplishing the present disclosure. For example, but not by way of limitation, the number of protrusions present may be about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 125, about 150, about 175, about 200, about 225, about 250, about 275, about 300, about 325, about 350, about 375, about 400, about 425, about 450, about 500, about 525, about 550, about 575, about 600, about 625, about 650, about 675, about 700, about 725, about 750, about 775, about 800, about 825, about 850, about 875, about 900, about 925, about 950, about 975, or greater than or equal to about 1,000 protrusions, as well as a range formed of two of any of the above values (i.e., a range of from about 1 to about 100 protrusions, etc.), and a range that combines two integers that fall between two of the above-referenced values (i.e., a range of from about 33 to about 98 protrusions, etc.).

The protrusions may be any shape capable of accomplishing the present disclosure. In addition, the protrusions may be the same shape, different shapes, and/or have the same or different dimensions. In one non-limiting embodiment, the protrusions(s) 90 may be of any height (i.e., the distance from the second surface 88 of the polymerized hydrogel 84 to the patient's epidermal layer) capable of accomplishing the present disclosure. Non-limiting examples of protrusion heights that may be utilized in accordance with the present disclosure include a height of about 0.1 millimeter, about 0.2 millimeter, about 0.3 millimeter, about 0.4 millimeter, about 0.5 millimeter, about 0.6 millimeter, about 0.7 millimeter, about 0.8 millimeter, about 0.9 millimeter, about 1.0 millimeter, about 1.1 millimeter, about 1.2 millimeter, about 1.3 millimeter, about 1.4 millimeter, about 1.5 millimeter, about 1.6 millimeter, about 1.7 millimeter, about 1.8 millimeter, about 1.9 millimeter, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, or greater than or equal to about 3.5 millimeters. In one non-limiting embodiment, the protrusions(s) 90 may be any diameter capable of accomplishing the present disclosure, including, but not limited to, a diameter of about 0.1 millimeter, about 0.2 millimeter, about 0.3 millimeter, about 0.4 millimeter, about 0.5 millimeter, about 0.6 millimeter, about 0.7 millimeter, about 0.8 millimeter, about 0.9 millimeter, about 1.0 millimeter, about 1.1 millimeter, about 1.2 millimeter, about 1.3 millimeter, about 1.4 millimeter, about 1.5 millimeter, about 1.6 millimeter, about 1.7 millimeter, about 1.8 millimeter, about 1.9 millimeter, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, or greater than or equal to about 3.5 millimeters, as well as a range formed of two of any of the above values (i.e., a range of from about 0.1 mm to about 3 mm, etc.), and a range that combines two integers that fall between two of the above-referenced values (i.e., a range of from about 1.05 mm to about 3.15 mm, etc.).

When the polymerized hydrogel layer 84 comprises more than one protrusion, the multiple protrusions may have the same or different shapes and dimension(s). In one non-limiting embodiment, each or all of the protrusion(s) may be tapered wherein the portion of the protrusion(s) formed on the second surface 88 of the polymerized hydrogel 84 may have a larger diameter than the portion of the protrusion(s) contacting the patient's epidermal layer—or vice versa.

In the non-limiting embodiment shown in FIGS. 6A-6B, about 50% of the polymerized hydrogel layer 84 adheres to the patient's epidermal layer and comprises the multiple protrusions 90.

Referring now to FIGS. 7-10, shown therein are non-limiting embodiments and configurations of polymerized hydrogels that have modifications therein that can be utilized in accordance with the present disclosure. FIGS. 7, 8, 9, and 10 illustrate polymerized hydrogels 100, 110, 120, and 130, respectively. The polymerized hydrogels 100, 110, 120, and 130 have a plurality of indentations 102, 112, 124, and 134, respectively, formed in a second surface 104, 114, 124, and 134, respectively thereof. The indentations may form a recess, well, or channel within the polymerized hydrogel, such as (but not limited to), the indentation 112A of the polymerized hydrogel 110 of FIG. 8 or the indentation 132 of the polymerized hydrogel 130 of FIG. 10. Alternatively, the indentations may form a channel that extends to an edge of the polymerized hydrogel, such as (but not limited to), the indentation 102 of the polymerized hydrogel 100 of FIG. 7, the indentation 112B of the polymerized hydrogel 110 of FIG. 8, and the indentation 122 of the polymerized hydrogel 120 of FIG. 9.

Each of the indentations/channels allows for the introduction and flow of liquid hydrogel and/or air underneath the polymerized hydrogel layer, thereby allowing for the benefits of the present disclosure as described elsewhere herein.

When liquid hydrogel is disposed within any of the perforations/indentations/recesses/channels of the polymerized hydrogels, the liquid may fill only a portion of the perforations/indentations/recesses/channels. Alternatively (and/or in addition thereto), the liquid may substantially fill the perforations/indentations/recesses/channels. In yet another alternative, the perforations/indentations/recesses/channels may contain excess liquid hydrogel that extends beyond the perforations/indentations/recesses/channels in response to application to a patient's skin; the presence of excess liquid hydrogel will decrease resistivity of the system.

For example, the addition of a drop of CARRASYN® V hydrogel wound dressing (Medline Industries, Inc., Northfield, Ill.) to an existing array (as shown in FIG. 3) being operated at a max current of 3489 mA for 15 minutes reduced the array resistance from 45 Ohm-in to 36 Ohm-in.

Figure 11:
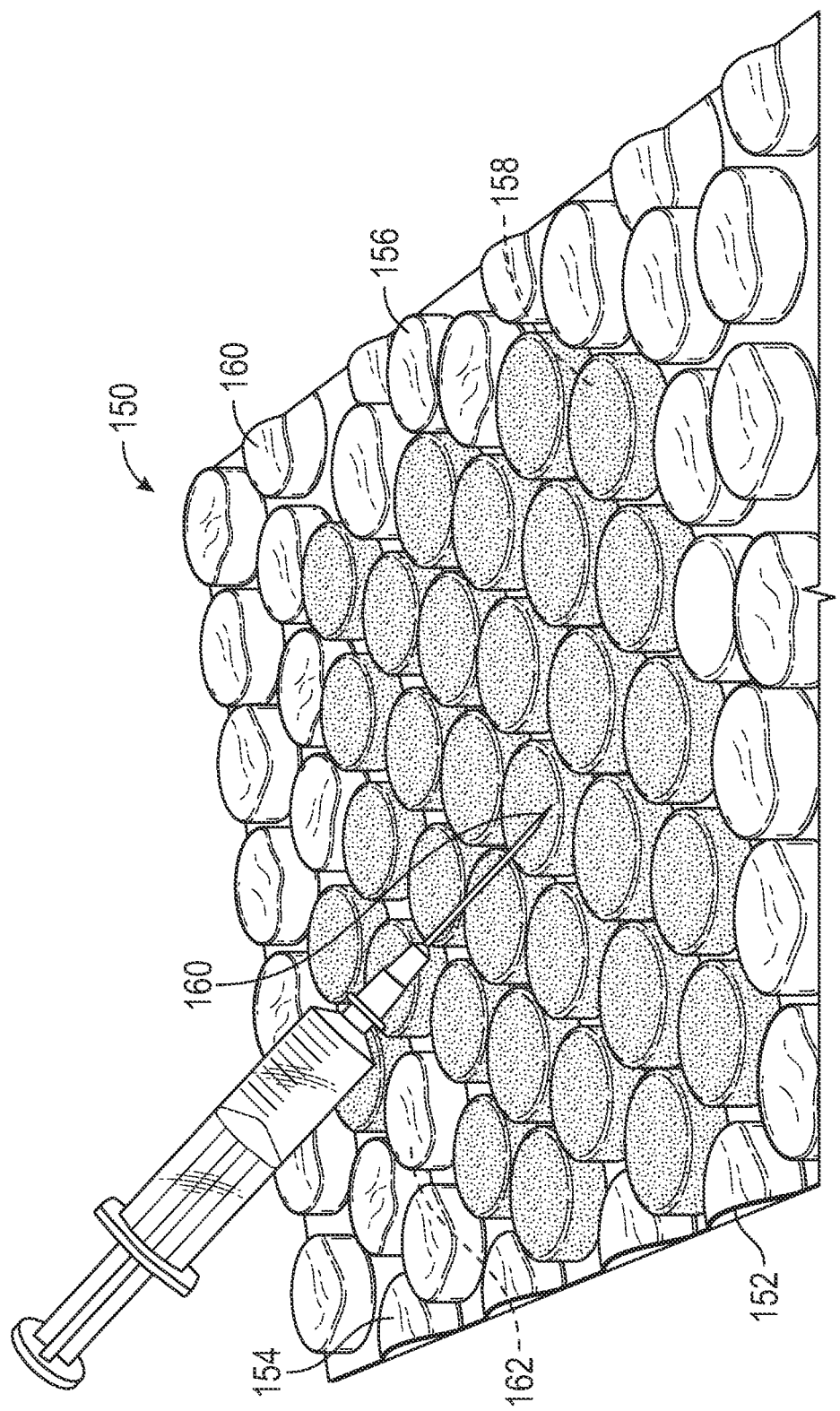
FIG. 11 is a schematic illustration of a polymerized conductive gel having a plurality of compartments extending therefrom, wherein at least a portion of the compartments contain liquid conductive gel.

FIG. 11 contains another non-limiting embodiment and configuration of a modified polymerized hydrogel that can be utilized in accordance with the present disclosure. The polymerized hydrogel 150 is similar to (and can be constructed in the same manner as) the polymerized hydrogels described herein before and has a first surface 152 for adherence to the lower surface of the high capacitance layer of the electrode, and a second surface 154 for application to a patient's skin. The second surface 154 has a plurality of compartments 156 extending therefrom, and at least a portion of the plurality of compartments 156 contains a liquid conductive hydrogel 158 disposed therein. In particular, each of the plurality of compartments 156 has a sidewall 160 that is attached to the second surface 154 of the polymerized hydrogel 150 and that surrounds and encompasses an inner retaining space 162 in which the liquid conductive hydrogel 158 is disposed.

At least a portion of the sidewall 160 of the liquid hydrogel-containing compartment(s) 156 is formed of a material that allows release of the liquid conductive hydrogel 158 therefrom, such as (but not limited to), in response to application of an amount of pressure thereto and/or released over time (i.e., a controlled release-type material).

The sidewall 160 of the compartment 156 may be provided with any mechanism known in the art or otherwise described herein that allows for release of the liquid conductive hydrogel 158 therefrom at a desired time and/or under desired conditions. For example (but not by way of limitation), the material from which the sidewall 160 of the at least one compartment 156 is formed may have one or more pores 160 formed therein that allows release of the liquid conductive hydrogel 158 therefrom in response to pressure and/or time. Alternatively, the thickness of the material from which at least a portion of the sidewall 160 of the compartment 156 is formed may be sufficiently thin so as to allow for at least a partial rupturing of the sidewall 160 and subsequent release of the liquid conductive hydrogel 158 in response to pressure (such as, but not limited to, the pressure of applying an electrode to which the polymerized hydrogel 150 is attached to a patient's skin). The material from which the sidewall 160 is formed may also comprise one or more other elements that are well known in the art to assist in rupturing at least a portion of a sidewall (i.e., perforations, score lines, etc.).

While the polymerized hydrogel 150 is depicted as having a plurality of compartments 156 on the second surface 154 thereof, this configuration is not to be construed as limiting of the scope of the present disclosure. It will be understood that the polymerized hydrogel 150 may contain only a single compartment 156 thereon, or the polymerized hydrogel 150 may be provided with multiple compartments 156 thereon in the same or in a different shape and/or configuration than that shown in FIG. 11. As such, the shape and configuration shows in FIG. 11 is solely for purposes of example only.

In addition, when two or more compartments 156 are present, they may have the same mechanism for release of the liquid conductive hydrogel 158 therefrom, or the two or more compartments 156 may include two or more different mechanisms for release. For example (but not by way of limitation), two or more of the compartments 158 may be formed in the same manner such that the liquid hydrogel 158 is released from both at substantially the same time/rate. Alternatively, two or more of the liquid hydrogel-containing compartments 156 may be formed of different materials and/or different thicknesses of material (and/or with and without pores) so as to allow release of the liquid conductive hydrogel 158 at different amounts of pressure and/or over a desired period of time (i.e., controlled time release). In yet another alternative, the controlled release of the liquid conductive hydrogel 158 from the compartments 156 may be obtained simply by only applying pressure to certain portion(s) of the polymerized hydrogel 150 at a given time.

The number of compartment(s) 156 present on the second surface 154 of the polymerized hydrogel layer 150 may be any number of compartments capable of accomplishing the inventive concept(s). For example, but not by way of limitation, the number of compartments 156 present may be about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 125, about 150, about 175, about 200, about 225, about 250, about 275, about 300, about 325, about 350, about 375, about 400, about 425, about 450, about 500, about 525, about 550, about 575, about 600, about 625, about 650, about 675, about 700, about 725, about 750, about 775, about 800, about 825, about 850, about 875, about 900, about 925, about 950, about 975, or greater than or equal to about 1,000 compartments, as well as a range formed of two of any of the above values (i.e., a range of from about 1 to about 100 compartments, etc.), and a range that combines two integers that fall between two of the above-referenced values (i.e., a range of from about 33 to about 98 compartments, etc.).

The compartments 156 may have any shape capable of accomplishing the inventive concept(s). In addition, the compartments 156 may have the same shape, different shapes, and/or have the same or different dimensions. In one non-limiting embodiment, the compartment(s) 156 may be of any height capable of accomplishing the present inventive concept(s). Non-limiting examples of compartment heights that may be utilized in accordance with the present disclosure include a height of about 0.1 millimeter, about 0.2 millimeter, about 0.3 millimeter, about 0.4 millimeter, about 0.5 millimeter, about 0.6 millimeter, about 0.7 millimeter, about 0.8 millimeter, about 0.9 millimeter, about 1.0 millimeter, about 1.1 millimeter, about 1.2 millimeter, about 1.3 millimeter, about 1.4 millimeter, about 1.5 millimeter, about 1.6 millimeter, about 1.7 millimeter, about 1.8 millimeter, about 1.9 millimeter, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, or greater than or equal to about 3.5 millimeters. In one non-limiting embodiment, the compartments 156 may be any diameter capable of accomplishing the present disclosure, including, but not limited to, a diameter of about 0.1 millimeter, about 0.2 millimeter, about 0.3 millimeter, about 0.4 millimeter, about 0.5 millimeter, about 0.6 millimeter, about 0.7 millimeter, about 0.8 millimeter, about 0.9 millimeter, about 1.0 millimeter, about 1.1 millimeter, about 1.2 millimeter, about 1.3 millimeter, about 1.4 millimeter, about 1.5 millimeter, about 1.6 millimeter, about 1.7 millimeter, about 1.8 millimeter, about 1.9 millimeter, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, or greater than or equal to about 3.5 millimeters, as well as a range formed of two of any of the above values (i.e., a range of from about 0.1 mm to about 3 mm, etc.), and a range that combines two integers that fall between two of the above-referenced values (i.e., a range of from about 1.05 mm to about 3.15 mm, etc.).

When the liquid conductive hydrogel 158 is present in the inner retaining space 162 of the compartment 156, the liquid conductive hydrogel 158 may be present at a volume that substantially fills the inner retaining space 162. Alternatively, the liquid conductive hydrogel 158 may be present at a volume that only partially fills the inner retaining space 162 of the compartment 156.

NON-LIMITING ILLUSTRATIVE EMBODIMENTS OF THE INVENTIVE CONCEPT(S)

Illustrative Embodiment 1

An assembly, comprising: at least one electrode; a polymerized conductive hydrogel for placement between the at least one electrode and a patient's skin, the polymerized hydrogel having a first surface and a second surface, wherein the first surface of the polymerized hydrogel adheres to a surface of the at least one electrode and the second surface of the polymerized hydrogel is for application to a patient's skin; and a liquid conductive hydrogel disposed on at least a portion of the second surface of the polymerized hydrogel.

Illustrative Embodiment 2

The assembly of illustrative embodiment 1, further comprising a liner disposed on the liquid hydrogel and covering at least a portion of the second surface of the polymerized hydrogel.

Illustrative Embodiment 3

The assembly of any of illustrative embodiments 1-2, wherein the polymerized hydrogel is semi-solid.

Illustrative Embodiment 4

The assembly of any of illustrative embodiments 1-3, wherein an osmolality of the liquid hydrogel is substantially identical to an osmolality of the polymerized hydrogel or varies therefrom by less than about 20%.

Illustrative Embodiment 5

The assembly of any of illustrative embodiments 1-4, wherein the polymerized hydrogel is devoid of perforations.

Illustrative Embodiment 6

The assembly of any of illustrative embodiments 1-5, wherein the polymerized conductive hydrogel comprises at least one modification that extends inwardly or outwardly from the second surface thereof.

Illustrative Embodiment 7

The assembly of illustrative embodiment 6, wherein the at least one modification is selected from the group consisting of: a perforation extending inwardly from the second surface to the first surface thereof and through the polymerized conductive hydrogel; a recess, channel, or well extending inwardly from the second surface of the polymerized conductive hydrogel; a plurality of protrusions extending outwardly from the second surface thereof, and wherein two or more protrusions form a recess, channel, or well therebetween; and combinations thereof.

Illustrative Embodiment 8

The assembly of illustrative embodiment 7, wherein at least a portion of the liquid hydrogel is disposed in or associated with the at least one modification.

Illustrative Embodiment 9

The assembly of illustrative embodiment 8, wherein the polymerized conductive hydrogel comprises a plurality of modifications that extend inwardly or outwardly from the second surface thereof, and wherein the plurality of modifications has liquid hydrogel disposed therein or associated therewith.

Illustrative Embodiment 10

The assembly of illustrative embodiment 8, wherein the polymerized conductive hydrogel comprises a plurality of modifications that extend inwardly or outwardly from the second surface thereof, and wherein at least a portion of the plurality of modifications have liquid hydrogel disposed therein or associated therewith, while at least a portion of the plurality of modifications are substantially devoid of liquid hydrogel.

Illustrative Embodiment 11

The assembly of any of illustrative embodiments 6-10, wherein at least one of the modifications comprises at least one dermatological therapeutic agent disposed therein or associated therewith.

Illustrative Embodiment 12

The assembly of illustrative embodiment 11, wherein the dermatological therapeutic agent is selected from the group consisting of an anti-microbial agent, an antibiotic, an anti-viral agent, an anti-fungal agent, an anti-inflammatory agent, an anesthetic, an emollient, a cleansing agent, an astringent, and combinations thereof.

Illustrative Embodiment 13

A transducer array for a TTField-generating system, comprising: at least one assembly of any one of illustrative embodiments 1-12.

Illustrative Embodiment 14

The transducer array of illustrative embodiment 13, further defined as comprising a plurality of assemblies in a range of from about 3 assemblies to about 30 assemblies.

Illustrative Embodiment 15

A method, comprising: applying two or more of the transducer arrays of any of illustrative embodiments 13-14 to a skin of a patient; and generating an electric field for a period of time.

Illustrative Embodiment 16

The method of illustrative embodiment 15, wherein the electric field is an alternating electric field having a frequency in a range of from about 50 kHz to about 500 kHz for a period of time.

Illustrative Embodiment 17

A kit, comprising: a polymerized conductive hydrogel for application to a patient's skin and for placement between the patient's skin and at least one transducer array that generates an electric field (such as, but not limited to, an alternating electric field having a frequency in a range of from about 50 kHz to about 500 kHz), wherein the polymerized conductive hydrogel comprises a first surface and a second surface; and a liquid conductive hydrogel for disposal on at least a portion of the second surface of the polymerized hydrogel.

Illustrative Embodiment 18

The kit of illustrative embodiment 17, further comprising instructions for applying at least a portion of the liquid hydrogel to at least a portion of the polymerized hydrogel.

Illustrative Embodiment 19

The kit of illustrative embodiment 17 or 18, wherein the polymerized hydrogel is semi-solid.

Illustrative Embodiment 20

The kit of any of illustrative embodiments 17-19, wherein an osmolality of the liquid hydrogel is substantially identical to an osmolality of the polymerized hydrogel or varies therefrom by less than about 20%.

Illustrative Embodiment 21

The kit of any of illustrative embodiments 17-20, wherein the polymerized hydrogel is devoid of perforations.

Illustrative Embodiment 22

The kit of any of illustrative embodiments 17-21, wherein the polymerized conductive hydrogel comprises at least one modification that extends inwardly or outwardly from the second surface thereof.

Illustrative Embodiment 23

The kit of illustrative embodiment 22, wherein the at least one modification is selected from the group consisting of: a perforation extending inwardly from the second surface to the first surface thereof and through the polymerized conductive hydrogel; a recess, channel, or well extending inwardly from the second surface of the polymerized conductive hydrogel; a plurality of protrusions extending outwardly from the second surface thereof, and wherein two or more protrusions form a recess, channel, or well therebetween; and combinations thereof.

Illustrative Embodiment 24

The kit of illustrative embodiment 23, wherein at least a portion of the liquid hydrogel is disposed in or associated with the at least one modification.

Illustrative Embodiment 25

The kit of illustrative embodiment 24, wherein the polymerized conductive hydrogel comprises a plurality of modifications that extend inwardly or outwardly from the second surface thereof, and wherein the plurality of modifications has liquid hydrogel disposed therein or associated therewith.

Illustrative Embodiment 26

The kit of illustrative embodiment 24, wherein the polymerized conductive hydrogel comprises a plurality of modifications that extend inwardly or outwardly from the second surface thereof, and wherein at least a portion of the plurality of modifications have liquid hydrogel disposed therein or associated therewith, while at least a portion of the plurality of modifications are substantially devoid of liquid hydrogel.

Illustrative Embodiment 27

The kit of any of illustrative embodiments 17-26, further comprising at least one dermatological therapeutic agent.

Illustrative Embodiment 28

The kit of illustrative embodiment 27, wherein the dermatological therapeutic agent is selected from the group consisting of an anti-microbial agent, an antibiotic, an anti-viral agent, an anti-fungal agent, an anti-inflammatory agent, an anesthetic, an emollient, a cleansing agent, an astringent, and combinations thereof.

Illustrative Embodiment 29

The kit of any of illustrative embodiments 17-28, further comprising at least one pair of transducer arrays that generates an alternating electric field having a frequency in a range of from about 50 kHz to about 500 kHz upon application to a patient's skin in combination with the polymerized hydrogel and the liquid hydrogel.

Illustrative Embodiment 30

The kit of any of illustrative embodiments 17-29, further comprising at least one pair of transducer arrays that generates an alternating electric field having a frequency in a range of from about 50 kHz to about 500 kHz upon application to a patient's skin in combination with the polymerized hydrogel and the liquid hydrogel.

Illustrative Embodiment 31

The kit of any of illustrative embodiments 17-30, wherein the kit has a shelf life of at least about six months.

Illustrative Embodiment 32

The kit of any of illustrative embodiments 17-31, further comprising a sealed packaging in which the polymerized conductive hydrogel and the liquid conductive hydrogel are disposed, wherein the sealed packaging is substantially impermeable to air and substantially impermeable to light.

Illustrative Embodiment 33

An assembly, comprising: at least one electrode; a polymerized conductive hydrogel for placement between the at least one electrode and a patient's skin, the polymerized hydrogel having a first surface and a second surface, wherein the first surface of the polymerized hydrogel adheres to a surface of the electrode and the second surface of the polymerized hydrogel is for application to a patient's skin; and at least one compartment extending from the second surface of the polymerized conductive hydrogel, the at least one compartment comprising a sidewall that is attached to the second surface of the polymerized conductive hydrogel and that surrounds and encompasses an inner retaining space in which a liquid conductive hydrogel is disposed, and wherein at least a portion of the sidewall of the at least one compartment is formed of a material that allows release of the liquid conductive hydrogel from the at least one compartment.

Illustrative Embodiment 34

The assembly of illustrative embodiment 33, wherein the liquid conductive hydrogel is released from the at least one compartment in response to application of an amount of pressure thereto.

Illustrative Embodiment 35

The assembly of illustrative embodiment 33 or 34, wherein the liquid conductive hydrogel is released from the at least one compartment over time.

Illustrative Embodiment 36

The assembly of any of illustrative embodiments 33-35, wherein at least a portion of the material from which the sidewall of the at least one compartment is formed comprises at least one pore for release of the liquid conductive hydrogel.

Illustrative Embodiment 37

The assembly of illustrative embodiment 36, wherein the sidewall of the at least one compartment comprises a plurality of pores.

Illustrative Embodiment 38

The assembly of any of illustrative embodiments 33-35, wherein the material from which the sidewall of the at least one compartment is formed is devoid of pores.

Illustrative Embodiment 39

The assembly of any of illustrative embodiments 33-38, wherein the at least one compartment is further defined as a plurality of compartments, each containing liquid conductive hydrogel disposed therein.

Illustrative Embodiment 40

The assembly of illustrative embodiment 39, wherein the thicknesses of the material from which the sidewalls of at least two of the plurality of compartments are formed differ from one another so as to allow release of the liquid conductive hydrogel at different amounts of pressure.

Illustrative Embodiment 41

The assembly of illustrative embodiment 39, wherein the sidewalls of each of the plurality of compartments is formed of the same thickness of material as the sidewalls of the other compartments so that liquid conductive hydrogel is released from each compartment in response to substantially the same amount of pressure.

Illustrative Embodiment 42

The assembly of any of illustrative embodiments 33-41, wherein the at least one electrode generates an alternating electric field having a frequency in a range from about 50 kHz to about 500 kHz.

Illustrative Embodiment 43

The assembly of any of illustrative embodiments 33-42, further comprising a liner disposed on the liquid hydrogel and covering at least a portion of the second surface of the polymerized hydrogel and the at least one compartment.

Illustrative Embodiment 44

The assembly of any of illustrative embodiments 33-43, wherein the polymerized hydrogel is semi-solid.

Illustrative Embodiment 45

The assembly of any of illustrative embodiments 33-44, wherein an osmolality of the liquid hydrogel is substantially identical to an osmolality of the polymerized hydrogel or varies therefrom by less than about 20%.

Illustrative Embodiment 46

The assembly of any of illustrative embodiments 33-45, wherein the polymerized conductive hydrogel comprises at least one modification that extends inwardly or outwardly from the second surface thereof.

Illustrative Embodiment 47

The assembly of illustrative embodiment 46, wherein the at least one modification is selected from the group consisting of: a perforation extending inwardly from the second surface to the first surface thereof and through the polymerized conductive hydrogel; a recess, channel, or well extending inwardly from the second surface of the polymerized conductive hydrogel; a plurality of compartments extending outwardly from the second surface thereof, and wherein two or more compartments form a recess, channel, or well therebetween; and combinations thereof.

Illustrative Embodiment 48

The assembly of any of illustrative embodiments 33-47, further comprising at least one dermatological therapeutic agent disposed in or associated with at least one of the second surface of the polymerized conductive hydrogel and the inner retaining space of the at least one compartment containing the liquid conductive hydrogel.

Illustrative Embodiment 49

The assembly of illustrative embodiment 48, wherein the dermatological therapeutic agent is selected from the group consisting of an anti-microbial agent, an antibiotic, an anti-viral agent, an anti-fungal agent, an anti-inflammatory agent, an anesthetic, an emollient, a cleansing agent, an astringent, and combinations thereof.

Illustrative Embodiment 50

The assembly of any of illustrative embodiments 33-49, further defined as comprising at least two compartments, wherein the inner retaining space of at least one of the compartments contains liquid conductive hydrogel and the inner retaining space of the other compartment contains at least one dermatological therapeutic agent.

Illustrative Embodiment 51

The assembly of illustrative embodiment 50, wherein the dermatological therapeutic agent is selected from the group consisting of an anti-microbial agent, an antibiotic, an anti-viral agent, an anti-fungal agent, an anti-inflammatory agent, an anesthetic, an emollient, a cleansing agent, an astringent, and combinations thereof.

Illustrative Embodiment 52

A transducer array for a TTField-generating system, comprising: at least one assembly of any one of illustrative embodiments 33-51.

Illustrative Embodiment 53

The transducer array of illustrative embodiment 52, further defined as comprising a plurality of assemblies in a range of from about 3 assemblies to about 30 assemblies.

Illustrative Embodiment 54

A method, comprising: applying two or more of the transducer arrays of illustrative embodiment 52 or 53 to a skin of a patient; and generating an electric field fora period of time.

Illustrative Embodiment 55

The method of illustrative embodiment 54, wherein the electric field is an alternating electric field having a frequency in a range of from about 50 kHz to about 500 kHz for a period of time.

Illustrative Embodiment 56

A kit, comprising: at least one assembly of any one of illustrative embodiments 33-51.

Illustrative Embodiment 57

The kit of illustrative embodiment 56, further comprising instructions for applying the at least one assembly to a patient's skin.

Illustrative Embodiment 58

The kit of illustrative embodiment 56 or 57, further comprising at least one dermatological therapeutic agent.

Illustrative Embodiment 59

The kit of illustrative embodiment 58, wherein the dermatological therapeutic agent is selected from the group consisting of an anti-microbial agent, an antibiotic, an anti-viral agent, an anti-fungal agent, an anti-inflammatory agent, an anesthetic, an emollient, a cleansing agent, an astringent, and combinations thereof.

Illustrative Embodiment 60

The kit of any of illustrative embodiments 56-59, further comprising at least one pair of transducer arrays that generates an alternating electric field having a frequency in a range of from about 50 kHz to about 500 kHz upon application to a patient's skin in combination with the polymerized hydrogel and the liquid hydrogel.

Illustrative Embodiment 61

The kit of any of illustrative embodiments 56-60, wherein the kit has a shelf life of at least about six months.

Illustrative Embodiment 62

The kit of any of illustrative embodiments 56-61, further comprising a sealed packaging in which the assembly is disposed, wherein the sealed packaging is substantially impermeable to air and substantially impermeable to light.

While the attached disclosures describe the inventive concept(s) in conjunction with the specific experimentation, results, and language set forth hereinafter, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. An assembly, comprising:
   at least one electrode;
   a polymerized conductive hydrogel for placement between the at least one electrode and a patient's skin, the polymerized hydrogel having a first surface and a second surface, wherein the first surface of the polymerized hydrogel adheres to a surface of the at least one electrode and the second surface of the polymerized hydrogel is for application to a patient's skin; and
   a liquid conductive hydrogel disposed on at least a portion of the second surface of the polymerized hydrogel.

2. The assembly of claim 1, further comprising a liner disposed on the liquid conductive hydrogel and covering at least a portion of the second surface of the polymerized hydrogel.

3. The assembly of claim 1, wherein an osmolality of the liquid conductive hydrogel is substantially identical to an osmolality of the polymerized hydrogel or varies therefrom by less than about 20%.

4. The assembly of claim 1, wherein the polymerized conductive hydrogel comprises at least one modification that extends inwardly or outwardly from the second surface thereof, and wherein the at least one modification is selected from the group consisting of:
   a perforation extending inwardly from the second surface to the first surface thereof and through the polymerized conductive hydrogel;
   a recess, channel, or well extending inwardly from the second surface of the polymerized conductive hydrogel;
   a plurality of protrusions extending outwardly from the second surface thereof, and wherein two or more protrusions form a recess, channel, or well therebetween;
   at least one compartment extending from the second surface of the polymerized conductive hydrogel, the at least one compartment comprising a sidewall that is attached to the second surface of the polymerized conductive hydrogel and that surrounds and encompasses an inner retaining space in which the liquid conductive hydrogel is disposed, and wherein at least a portion of the sidewall of the at least one compartment is formed of a material that allows release of the liquid conductive hydrogel from the at least one compartment; and
   combinations thereof.

5. The assembly of claim 4, wherein at least a portion of the liquid conductive hydrogel is disposed in or associated with the at least one modification.

6. The assembly of claim 5, wherein the polymerized conductive hydrogel comprises a plurality of modifications that extend inwardly or outwardly from the second surface thereof, and wherein at least a portion of the plurality of modifications have liquid conductive hydrogel disposed therein or associated therewith, while at least a portion of the plurality of modifications are substantially devoid of the liquid conductive hydrogel.

7. The assembly of claim 6, wherein at least one of the plurality of modifications comprises at least one dermatological therapeutic agent disposed therein or associated therewith, wherein the dermatological therapeutic agent is selected from the group consisting of an anti-microbial agent, an antibiotic, an anti-viral agent, an anti-fungal agent, an anti-inflammatory agent, an anesthetic, an emollient, a cleansing agent, an astringent, and combinations thereof.

8. A transducer array for a tumor treating field (TTField)-generating system, comprising:
   at least one assembly of claim 1.

9. The transducer array of claim 8, further defined as comprising a plurality of assemblies of claim 1, wherein the plurality of assemblies is in a range of from about 3 assemblies to about 30 assemblies.

10. A method, comprising:
    applying two or more transducer arrays of claim 8 to a skin of a patient; and
    generating an electric field for a period of time.

11. The method of claim 10, wherein the the two or more transducer arrays cooperate to generate an alternating electric field having a frequency in a range of from about 50 kHz to about 500 kHz.

12. A kit, comprising:
    a polymerized conductive hydrogel for application to a patient's skin and for placement between the patient's skin and at least one transducer array that generates an electric field, wherein the polymerized conductive hydrogel comprises a first surface and a second surface; and
    a liquid conductive hydrogel for disposal on at least a portion of the second surface of the polymerized hydrogel.

13. The kit of claim 12, further comprising at least one of:
    instructions for applying at least a portion of the liquid conductive hydrogel to at least a portion of the polymerized hydrogel;
    at least one dermatological therapeutic agent selected from the group consisting of an anti-microbial agent, an antibiotic, an anti-viral agent, an anti-fungal agent, an anti-inflammatory agent, an anesthetic, an emollient, a cleansing agent, an astringent, and combinations thereof; and
    a sealed packaging in which the polymerized conductive hydrogel and the liquid conductive hydrogel are disposed, wherein the sealed packaging is substantially impermeable to air and substantially impermeable to light.

14. The kit of claim 12, wherein an osmolality of the liquid conductive hydrogel is substantially identical to an osmolality of the polymerized hydrogel or varies therefrom by less than about 20%.

15. The kit of claim 12, wherein the polymerized conductive hydrogel comprises at least one modification that extends inwardly or outwardly from the second surface thereof, and wherein the at least one modification is selected from the group consisting of:
    a perforation extending inwardly from the second surface to the first surface thereof and through the polymerized conductive hydrogel;
    a recess, channel, or well extending inwardly from the second surface of the polymerized conductive hydrogel;
    a plurality of protrusions extending outwardly from the second surface thereof, and wherein two or more protrusions form a recess, channel, or well therebetween;
    at least one compartment extending from the second surface of the polymerized conductive hydrogel, the at least one compartment comprising a sidewall that is attached to the second surface of the polymerized conductive hydrogel and that surrounds and encompasses an inner retaining space in which the liquid conductive hydrogel is disposed, and wherein at least a portion of the sidewall of the at least one compartment is formed of a material that allows release of the liquid conductive hydrogel from the at least one compartment; and combinations thereof.

16. The kit of claim 15, wherein at least a portion of the liquid conductive hydrogel is disposed in or associated with the at least one modification.

17. The kit of claim 16, wherein the polymerized conductive hydrogel comprises a plurality of modifications that extend inwardly or outwardly from the second surface thereof, and wherein at least a portion of the plurality of modifications have the liquid conductive hydrogel disposed therein or associated therewith, while at least a portion of the plurality of modifications are substantially devoid of the liquid conductive hydrogel.

18. The assembly of claim 4, wherein the at least one modification is the at least one compartment having the liquid conductive hydrogel disposed therein, and wherein the liquid conductive hydrogel is released from the at least one compartment in response to application of an amount of pressure thereto.

19. The assembly of claim 4, wherein the at least one modification is the at least one compartment having the liquid conductive hydrogel disposed therein, and wherein the liquid conductive hydrogel is released from the at least one compartment over time.

20. The assembly of claim 4, wherein the at least one compartment is further defined as a plurality of compartments, each containing the liquid conductive hydrogel disposed therein, and wherein the thicknesses of the material from which the sidewalls of at least two of the plurality of compartments are formed differ from one another so as to allow release of the liquid conductive hydrogel at different amounts of pressure.

* * * * *